(12) United States Patent
Cully et al.

(10) Patent No.: US 9,642,693 B2
(45) Date of Patent: May 9, 2017

(54) MEDICAL APPARATUS AND METHOD OF MAKING THE SAME

(75) Inventors: Edward H. Cully, Flagstaff, AZ (US); James Goepfrich, Flagstaff, AZ (US); Joanne Hopmeyer, Flaggstaff, AZ (US); Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 115 days.

(21) Appl. No.: 11/735,372

(22) Filed: Apr. 13, 2007

(65) Prior Publication Data

US 2008/0255587 A1   Oct. 16, 2008

(51) Int. Cl.
*A61B 17/08* (2006.01)
*A61F 2/04* (2013.01)
*A61F 5/00* (2006.01)

(52) U.S. Cl.
CPC .............. *A61F 2/04* (2013.01); *A61F 5/0003* (2013.01); *A61F 5/0076* (2013.01); *A61F 5/0089* (2013.01); *A61F 2002/044* (2013.01); *A61F 2220/0016* (2013.01)

(58) Field of Classification Search
CPC ............. A61F 5/0076; A61F 2002/045; A61B 17/1114
USPC ............... 606/153, 151, 157, 108; 623/23.65
See application file for complete search history.

(56) References Cited

U.S. PATENT DOCUMENTS

| | | | |
|---|---|---|---|
| 3,168,092 A | 2/1965 | Silverman | |
| 4,077,610 A | 3/1978 | Masuda | |
| 4,109,659 A | 8/1978 | Sheridan | |
| 4,133,315 A | 1/1979 | Berman et al. | |
| 4,134,405 A | 1/1979 | Smit | |
| 4,246,893 A | 1/1981 | Berson | |
| 4,254,774 A | 3/1981 | Boretos | |
| 4,271,839 A | 6/1981 | Fogarty et al. | |
| 4,315,509 A | 2/1982 | Smit | |

(Continued)

FOREIGN PATENT DOCUMENTS

| | | |
|---|---|---|
| EP | 0 103 481 | 3/1984 |
| EP | 0 584 352 | 3/1994 |

(Continued)

OTHER PUBLICATIONS

Milone L, Gagner M, Ueda K, et. al. Effect of a Polyethylene Endoluminal Duodeno-Jejunal Tube (EDJT) on Weight Gain: A Feasibility Study in a Porcine Model. Obesity Surgery May 2006; v16 n5 : 620-626.

(Continued)

*Primary Examiner* — Gregory Anderson
*Assistant Examiner* — Christina Lauer
(74) *Attorney, Agent, or Firm* — Amy L. Miller

(57) ABSTRACT

The invention relates to a medical apparatus including a device used in the treatment of weight loss, obesity and potentially other associated health problems, e.g., type II diabetes. The device is used to impede absorption of nutrients within the gastrointestinal tract, i.e., bypassing a portion of the gastrointestinal tract. The medical apparatus enables implantation of the device using minimally invasive techniques, such a transesophageal approach under visualization. The device may be implanted via a working channel of a medical scope, e.g., an endoscope or in combination with a medical scope.

28 Claims, 17 Drawing Sheets

(56) References Cited

U.S. PATENT DOCUMENTS

| | | | |
|---|---|---|---|
| 4,416,267 A | 11/1983 | Garren et al. | |
| 4,479,497 A | 10/1984 | Fogarty et al. | |
| 4,485,805 A | 12/1984 | Foster, Jr. | |
| 4,493,711 A | 1/1985 | Chin et al. | |
| 4,501,264 A | 2/1985 | Rockey | |
| 4,558,699 A | 12/1985 | Bashour | |
| 4,607,618 A | 8/1986 | Angelchik | |
| 4,641,653 A | 2/1987 | Rockey | |
| 4,694,827 A | 9/1987 | Weiner et al. | |
| 4,716,900 A | 1/1988 | Ravo et al. | |
| 4,723,547 A | 2/1988 | Kullas et al. | |
| 4,739,758 A | 4/1988 | Lai et al. | |
| 4,763,653 A | 8/1988 | Rockey | |
| 4,803,985 A | 2/1989 | Hill | |
| 4,863,440 A | 9/1989 | Chin | |
| 4,878,905 A | 11/1989 | Blass | |
| 4,886,062 A | 12/1989 | Wiktor | |
| 4,899,747 A | 2/1990 | Garren et al. | |
| 5,067,957 A | 11/1991 | Jervis | |
| 5,129,915 A | 7/1992 | Cantenys | |
| 5,171,305 A | 12/1992 | Schickling et al. | |
| 5,190,546 A | 3/1993 | Jervis | |
| 5,202,352 A | 4/1993 | Okada et al. | |
| 5,246,456 A | 9/1993 | Wilkinson | |
| 5,306,300 A | 4/1994 | Berry | |
| 5,603,950 A | 2/1997 | Ratjen et al. | |
| 5,628,786 A | 5/1997 | Banas et al. | |
| 5,662,713 A | 9/1997 | Andersen et al. | |
| 5,800,522 A | 9/1998 | Campbell et al. | |
| 5,817,015 A * | 10/1998 | Adair | 600/121 |
| 5,820,584 A | 10/1998 | Crabb | |
| 5,868,141 A | 2/1999 | Ellias | |
| 5,891,084 A * | 4/1999 | Lee | 604/521 |
| 5,925,683 A | 7/1999 | Park | |
| 6,039,721 A | 3/2000 | Johnson et al. | |
| 6,264,700 B1 | 7/2001 | Kilcoyne et al. | |
| 6,306,141 B1 | 10/2001 | Jervis | |
| 6,352,561 B1 * | 3/2002 | Leopold et al. | 623/1.23 |
| 6,355,056 B1 | 3/2002 | Pinheiro | |
| 6,395,019 B2 | 5/2002 | Chobotov | |
| 6,454,785 B2 | 9/2002 | De Hoyos Garza | |
| 6,530,951 B1 | 3/2003 | Bates et al. | |
| 6,551,350 B1 | 4/2003 | Thornton et al. | |
| 6,613,083 B2 | 9/2003 | Alt | |
| 6,645,242 B1 | 11/2003 | Quinn | |
| 6,656,219 B1 | 12/2003 | Wiktor | |
| 6,675,809 B2 | 1/2004 | Stack et al. | |
| 6,676,674 B1 | 1/2004 | Dudai | |
| 6,676,692 B2 | 1/2004 | Rabkin et al. | |
| 6,676,971 B2 | 1/2004 | Goupil et al. | |
| 6,677,318 B1 | 1/2004 | Beisel | |
| 6,699,276 B2 * | 3/2004 | Sogard et al. | 623/1.13 |
| 6,733,512 B2 | 5/2004 | McGhan | |
| 6,740,121 B2 | 5/2004 | Geitz | |
| 6,746,460 B2 | 6/2004 | Gannoe et al. | |
| 6,748,653 B2 | 6/2004 | Lindemans et al. | |
| 6,755,869 B2 | 6/2004 | Geitz | |
| 6,821,291 B2 | 11/2004 | Bolea et al. | |
| 6,869,438 B2 | 3/2005 | Chao | |
| 6,923,828 B1 | 8/2005 | Wiktor | |
| 6,946,002 B2 | 9/2005 | Geitz | |
| 7,025,791 B2 | 4/2006 | Levine et al. | |
| 7,037,344 B2 | 5/2006 | Kagan et al. | |
| 7,090,699 B2 | 8/2006 | Geitz | |
| 7,111,627 B2 | 9/2006 | Stack et al. | |
| 7,122,058 B2 | 10/2006 | Levine et al. | |
| 7,128,748 B2 | 10/2006 | Mooradian et al. | |
| 2001/0044595 A1 * | 11/2001 | Reydel et al. | 604/98.02 |
| 2002/0091395 A1 | 7/2002 | Gabbay | |
| 2002/0143387 A1 | 10/2002 | Soetikno et al. | |
| 2003/0040804 A1 | 2/2003 | Stack et al. | |
| 2003/0040808 A1 | 2/2003 | Stack et al. | |
| 2003/0109931 A1 | 6/2003 | Geitz | |
| 2003/0191476 A1 | 10/2003 | Smit | |
| 2003/0199805 A1 | 10/2003 | McWeeney | |
| 2003/0199989 A1 | 10/2003 | Stack et al. | |
| 2003/0199990 A1 | 10/2003 | Stack et al. | |
| 2004/0034407 A1 | 2/2004 | Sherry | |
| 2004/0039452 A1 | 2/2004 | Bessler | |
| 2004/0044354 A1 | 3/2004 | Gannoe et al. | |
| 2004/0092892 A1 | 5/2004 | Kagan et al. | |
| 2004/0092974 A1 | 5/2004 | Gannoe et al. | |
| 2004/0107030 A1 | 6/2004 | Levine et al. | |
| 2004/0116848 A1 * | 6/2004 | Gardeski et al. | 604/95.01 |
| 2004/0122503 A1 | 6/2004 | Campbell et al. | |
| 2004/0133147 A1 | 7/2004 | Woo | |
| 2004/0148034 A1 | 7/2004 | Kagan et al. | |
| 2004/0172142 A1 | 9/2004 | Stack et al. | |
| 2004/0172143 A1 | 9/2004 | Geitz | |
| 2004/0204768 A1 | 10/2004 | Geitz | |
| 2004/0219186 A1 | 11/2004 | Ayres | |
| 2004/0220682 A1 | 11/2004 | Levine et al. | |
| 2004/0249362 A1 | 12/2004 | Levine et al. | |
| 2005/0043817 A1 | 2/2005 | McKenna et al. | |
| 2005/0049718 A1 * | 3/2005 | Dann et al. | 623/23.65 |
| 2005/0075622 A1 | 4/2005 | Levine et al. | |
| 2005/0080395 A1 | 4/2005 | Levine et al. | |
| 2005/0080431 A1 | 4/2005 | Levine et al. | |
| 2005/0080491 A1 | 4/2005 | Levine et al. | |
| 2005/0085787 A1 | 4/2005 | Laufer | |
| 2005/0085923 A1 | 4/2005 | Levine et al. | |
| 2005/0096750 A1 | 5/2005 | Kagan et al. | |
| 2005/0125020 A1 | 6/2005 | Meade et al. | |
| 2005/0125075 A1 | 6/2005 | Meade et al. | |
| 2005/0131515 A1 | 6/2005 | Cully et al. | |
| 2005/0154448 A1 | 7/2005 | Cully et al. | |
| 2005/0177181 A1 | 8/2005 | Kagan et al. | |
| 2005/0192615 A1 | 9/2005 | Torre et al. | |
| 2005/0240279 A1 | 10/2005 | Kagan et al. | |
| 2005/0256587 A1 | 11/2005 | Egan | |
| 2005/0273060 A1 | 12/2005 | Levy et al. | |
| 2006/0009858 A1 | 1/2006 | Levine et al. | |
| 2006/0015125 A1 | 1/2006 | Swain | |
| 2006/0015171 A1 | 1/2006 | Armstrong | |
| 2006/0020254 A1 | 1/2006 | Hoffmann | |
| 2006/0025852 A1 | 2/2006 | Armstrong et al. | |
| 2006/0030949 A1 | 2/2006 | Geitz | |
| 2006/0058829 A1 | 3/2006 | Sampson et al. | |
| 2006/0064120 A1 | 3/2006 | Levine et al. | |
| 2006/0122691 A1 | 6/2006 | Richter | |
| 2006/0155312 A1 | 7/2006 | Levine et al. | |
| 2006/0161139 A1 | 7/2006 | Levine et al. | |
| 2006/0161172 A1 | 7/2006 | Levine et al. | |
| 2006/0161187 A1 | 7/2006 | Levine et al. | |
| 2006/0161241 A1 | 7/2006 | Barbut et al. | |
| 2006/0161265 A1 | 7/2006 | Levine et al. | |
| 2006/0212042 A1 | 9/2006 | Lamport et al. | |
| 2007/0005147 A1 | 1/2007 | Levine et al. | |
| 2007/0027548 A1 | 2/2007 | Levine et al. | |
| 2007/0083271 A1 | 4/2007 | Levine et al. | |
| 2007/0142896 A1 | 6/2007 | Anderson | |
| 2007/0156248 A1 | 7/2007 | Marco | |
| 2008/0015674 A1 * | 1/2008 | Austin | A61F 2/95 623/1.11 |

FOREIGN PATENT DOCUMENTS

| | | |
|---|---|---|
| EP | 0 815 806 | 6/1997 |
| EP | 0 819 412 | 1/1998 |
| EP | 1 700 580 | 9/2006 |
| FR | 2 862 525 | 5/2005 |
| JP | 2006507910 | 3/2006 |
| WO | 90/01879 | 3/1990 |
| WO | 98/27894 | 7/1998 |
| WO | 2004/041133 | 5/2004 |
| WO | WO2005/060869 | 7/2005 |
| WO | 2005/082296 | 9/2005 |
| WO | 2005/110280 | 11/2005 |
| WO | 2006/028925 | 3/2006 |
| WO | 2007136468 | 11/2007 |

(56) References Cited

FOREIGN PATENT DOCUMENTS

WO          2008030403      3/2008
WO    WO2008/127552    10/2008

OTHER PUBLICATIONS

Povoas, H Staplerless Laparoscopic Gastric Bypass: Not So Fast. Obesity Surgery Aug. 2006; v16 n8:1115-1116.
Satiety, Inc.'s New Transoral Procedure for Treating Obesity Shows Promising Results in First Clinical Trial. http://www.allbusiness.com/services/business-service/3939777-1.html Oct. 26, 2006.
Jun. 2, 2009; International Search Report and Written Opinion, International application No. PCT/US2009/002229.
Extended European Search Report dated Mar. 15, 2016 for EP 15 19 3323.

* cited by examiner

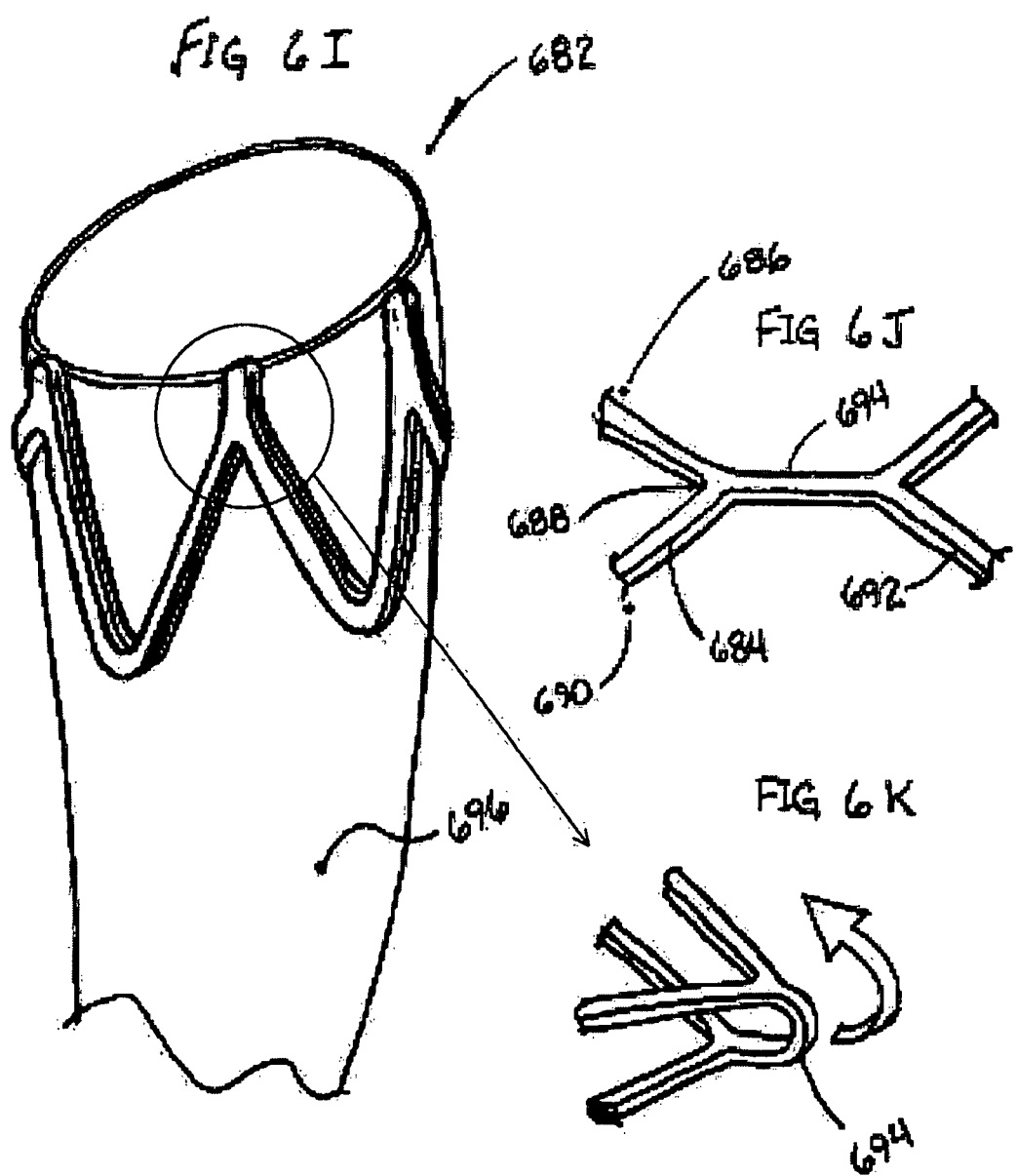

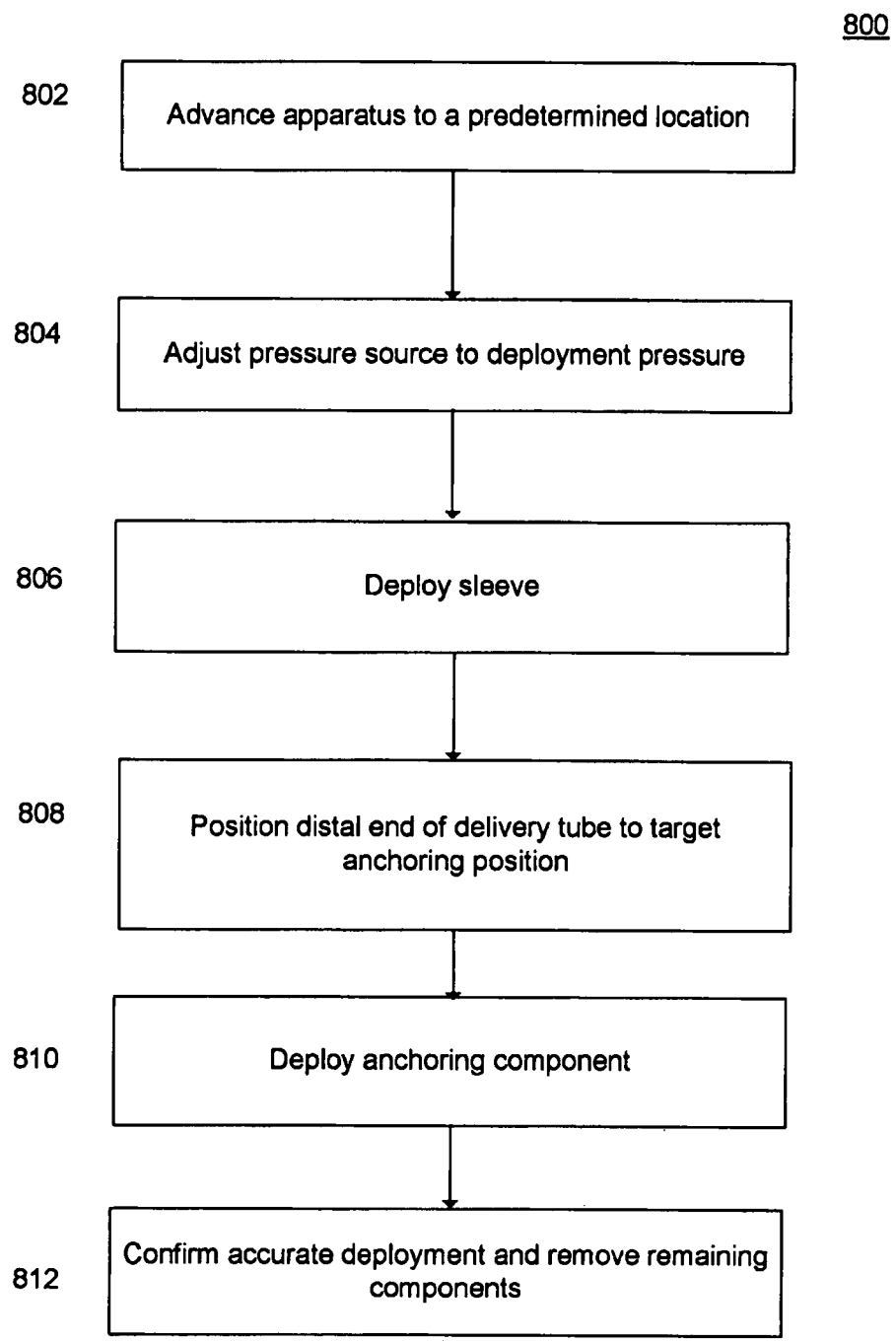

FIG. 9E
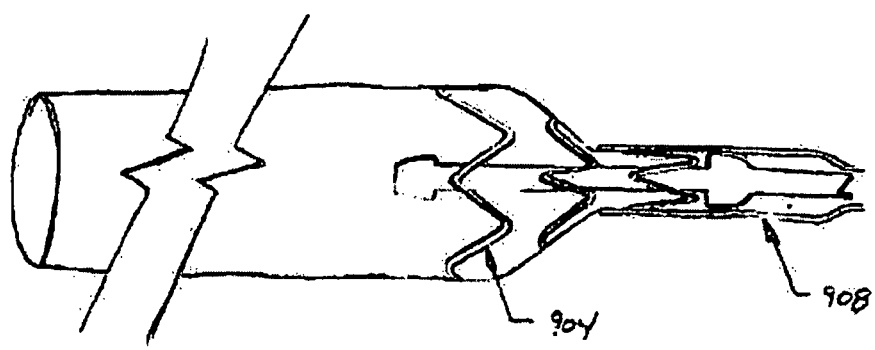
FIG. 9F
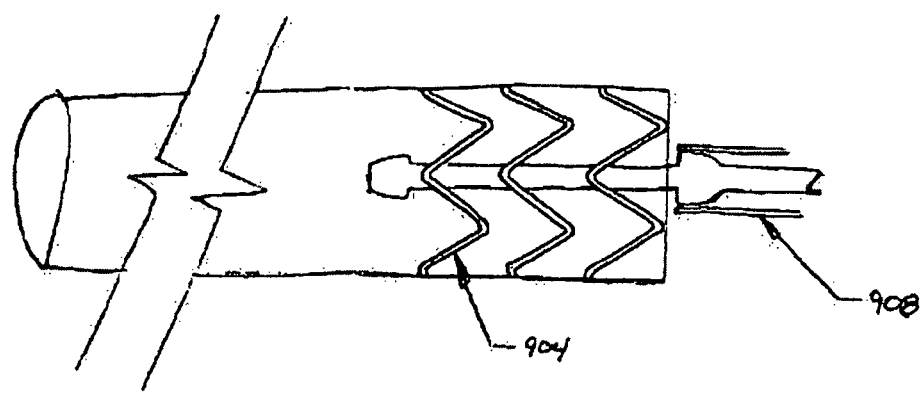
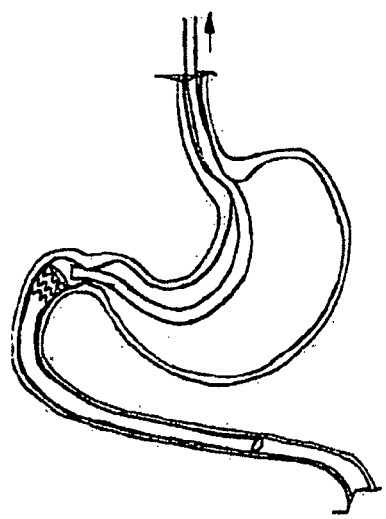
FIG. 9G

MEDICAL APPARATUS AND METHOD OF MAKING THE SAME

BACKGROUND OF THE INVENTION

Field of the Invention

The invention relates to a medical apparatus including a device used in the treatment of obesity and potentially other associated health problems, e.g., type II diabetes.

Discussion of the Related Art

Currently, obesity and related health problems are on the rise in the United States and in other industrialized countries. For example, the latest data from the National Center for Health Statistics show that 30 percent of U.S. adults 20 years of age and older—over 60 million people—are obese. Unfortunately, the increase in obesity rates is not limited to adults and the percentage of young people who are overweight has more than tripled since 1980. For example, among children and teens aged 6-19 years, 16 percent (over 9 million young people) are considered overweight.

Obesity may lead to a number of health problems including, for example, hypertension, dyslipidemia (e.g., high total cholesterol or high levels of triglycerides), diabetes (e.g., Type 2 diabetes), coronary heart disease, stroke, gallbladder disease, osteoarthritis, sleep apnea and respiratory problems, cancers (e.g., endometrial and breast), and other ill-health effects. See e.g., Kanders, B. S., et al., Weight loss outcome and health benefits associated with the Optifast program in the treatment of obesity. Int J Obes, 1989. 13: p. 131-134.

Currently, there are a number of devices and methods for treating obesity, including such surgical procedures as biliopancreatic diversion, silastic ring gastroplasty, jejunoileal bypass, gastric bypass, Roux-en-Y gastric bypass, gastroplasty, gastric banding, vertical banded gastroplasty, and staged procedures. Unfortunately, these procedures have a number of drawbacks including the possibility of severe complications associated with invasive and complicated procedures such as organ failure and even death.

Other less severe complications may include dumping syndrome. Dumping syndrome occurs when the contents of the stomach empty too quickly into the small intestine. The partially digested food draws excess fluid into the small intestine causing nausea, cramping, diarrhea, sweating, faintness, and/or palpitations. Dumping syndrome usually occurs after the consumption of too much simple or refined sugar by people who have had surgery to modify or remove part of the stomach.

SUMMARY OF THE INVENTION

The invention is directed to a medical apparatus to deliver a device that provides distinct advantages over the related art.

An advantage of the medical apparatus according to certain embodiments of the invention is to provide a device for treatment of obesity and potentially other associated health problems that is less invasive and may minimize complications of traditional surgical approaches.

Another advantage of the medical apparatus according to certain embodiments of the invention is its capability to permit delivery of a device using a medical scope, e.g., an endoscope.

Yet another advantage of the medical apparatus according to certain embodiments of the invention is its ability to enable full deployment of a sleeve across a tortuous anatomy.

Yet another advantage of the medical apparatus according to certain embodiments of the invention is its ability to allow deployment of the sleeve from a position not extending beyond an anchor placement. That is, the apparatus permits sleeve deployment from a location proximal to the furthest distal final location of the sleeve.

Additional features and advantages of the invention will be set forth in the description or may be learned by practice of the invention. These features and other advantages of the invention will be realized and attained by the structure particularly pointed out in the written description and claims hereof as well as the appended drawings.

To achieve these and other advantages and in accordance with the purpose of the invention, as embodied and broadly described, the medical apparatus according to certain embodiments of the invention includes a delivery tube having at least one lumen extending from a proximal end to a distal end of the delivery tube and a sleeve. The sleeve is substantially fully inverted and contained within at least a portion of one of the lumens. The sleeve may have an anchoring component attached to at least a portion of the delivery tube. The delivery tube may be sized such that it is capable of being inserted into a working channel of the medical scope. A sheath may be arranged over at least a portion of the delivery tube.

In another aspect the medical apparatus according to certain embodiments of the invention includes a sleeve comprising a fluoropolymer. An anchoring component is attached to at least a portion of said sleeve. A sleeve is substantially fully inverted and contained within at least one lumen of a delivery tube. Of course, the delivery tube may be configured so that it is capable of being inserted into the working channel of an endoscope. A sheath may be arranged over at least portion of the delivery tube.

In yet another aspect the medical apparatus according to certain embodiments of the invention includes a delivery tube having at least one lumen, a sleeve, and an anchoring component attached to at least a portion of said sleeve. The anchoring component is arranged on a distal portion of the delivery tube. At least a portion of the anchoring component is covered with a sheath. A cap is arranged over at least a portion of the sheath. The cap forms a space between a distal end of the delivery tube and the inside surface of the cap, such that the sleeve may be arranged in at least a portion of the space. Again, the delivery tube may be sized so that it is capable of being inserted into a working channel of an endoscope.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

In the drawings:

FIG. 6I illustrates an anchoring component according to another embodiment of the invention;

FIG. 6J illustrates an enlarged section view of a portion of the anchoring component shown in FIG. 6I;

FIG. 6K illustrates an enlarged section view of a portion of the anchoring component shown in FIG. 6I;

FIG. 8 illustrates a deployment flowchart according to an embodiment of the invention;

FIGS. 9A-9G illustrate a deployment procedure according to an embodiment of the invention.

DETAILED DESCRIPTION OF THE ILLUSTRATED EMBODIMENTS

Figure 1A:
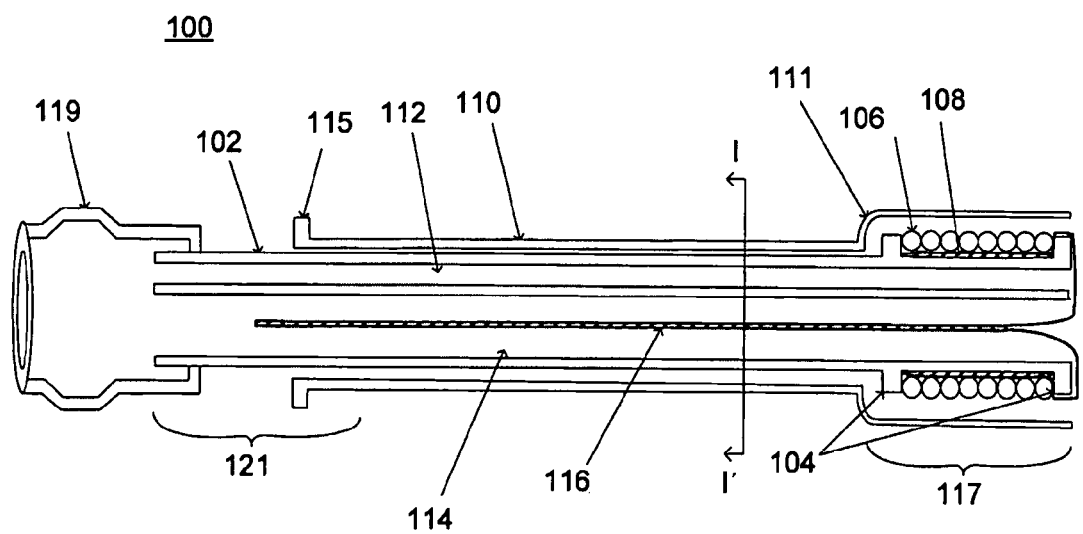
FIG. 1A illustrates a cross-sectional view of a medical apparatus according to an embodiment of the invention.

The invention relates to a novel medical apparatus including a device for treatment of obesity, weight loss, diabetes, and/or other obesity-associated health problems. The device is used to impede absorption of nutrients within the gastrointestinal tract, i.e., substantially isolating nutrients from a portion of the gastrointestinal tract. The medical apparatus enables implantation of the device using minimally invasive techniques, such a transesophageal approach under visualization. By way of example, the device may be implanted via a working channel of a medical scope, e.g., an endoscope or, in combination with a medical scope. Other techniques for implantation as known in the art may also be used with the apparatus, such as laparoscopic surgical techniques solely or in combination with the transesophageal techniques.

In one embodiment, the medical apparatus includes a device and a delivery tube configured to hold at least a portion of the device. The device includes a sleeve and an anchoring component attached to at least a portion of the sleeve. The anchoring component is optional and the sleeve may be attached to a patient via other attachment mechanisms. For example, the sleeve may be directly attached to a patient's anatomy by a variety of attachment mechanisms as known in the art, e.g., sutures, staples, adhesives, anchors, hooks, or combinations thereof and the like.

The delivery tube is used for holding and delivering the anchoring component and sleeve. For example, the delivery tube is capable of providing the anchoring component and sleeve to the anchoring component deployment site. The delivery tube includes at least one lumen extending throughout a portion of the delivery tube. The lumen may extend throughout the entire length of the delivery tube. In one embodiment, the outside diameter of the delivery tube ranges from about 16 mm to 3 mm or less, more preferably, it ranges from about 7 mm to 5 mm.

At least one of the lumens may be used for holding a portion of a sleeve. For example, a portion of the sleeve may be inverted inside a portion of the lumen. Inverted is defined as to at least partially turn inside out, i.e., where at least a portion of the external surface becomes an internal surface. The delivery tube may also include a connector arranged on an end of the delivery tube that is configured to permit a detachable connection to a medical pressurization source, e.g., a syringe or other device, that may be utilized in the everting process of the sleeve. The connector may be configured to be in fluid communication with a lumen.

The delivery tube may also include fixing components arranged on an inside portion, outside portion, or combination of inside and outside portions of the delivery tube. The fixing components are preferably arranged near a distal portion of the delivery tube. The fixing components are configured to impede the anchoring component from substantially moving along the axis of the delivery tube. That is, the fixing components may be used as stops to substantially prevent the anchoring component from movement past the stops in a longitudinal orientation, i.e., between the proximal and distal ends of the delivery tube.

Preferably, the fixing components are spaced far enough apart to allow the anchoring component to be arranged between the fixing components. The spacing may be in the range of about 2 cm to about 10 cm or more. The spacing and number of fixing components are dependent upon the type of anchoring component utilized. The fixing components may be constructed from the same material as the delivery tube. Preferably, the fixing components are constructed from a composite material, such as thermoplastic based materials or other suitable materials. In addition, these fixing components may be attached to the delivery tube such as fusing via a thermal process near a distal portion, such that, the fixing components become integral with the delivery tube.

The delivery tube may also include a plurality of lumens of different shapes and sizes extending partially or fully through the tube. For example, the delivery tube may include two lumens extending at least partially through the delivery tube. Moreover, the delivery tube may include a circular shaped lumens and an oval shaped lumen extending at least partially through the delivery tube. In one embodiment, the delivery tube includes a substantially circular lumen arranged adjacent to a substantially elliptical shaped lumen.

The delivery tube may be sized to have an outermost dimension that it is capable of fitting inside a working channel of a medical scope. The working channel is an internal lumen of the medical scope extending from a proximal to distal end of the scope. The working channel may not be straight along a length of a medical scope. For example, the working channel may have various angles or branches throughout its length and may not end at exactly the distal or proximal end, that is, it may be branched or ported off the side of the medical scope. The medical scope may be an endoscope or other suitable visualization instrument as known in the art. The working channel of an endoscope typically has an inside diameter ranging from about 10 mm or less. In a preferred embodiment, the delivery tube outside diameter ranges from about 7 mm to 5 mm.

Multiple constructs can be utilized to produce the delivery tube according to various embodiments of the invention. Preferably, the delivery tube is constructed from materials having good hoop strength and/or from materials that are not substantially diametrically adjustable. The delivery tube may be constructed from thermoplastic materials such as fluoropolymer materials, and the like. For example, the materials may include at least one of polytetrafluoroethylene (PTFE) polymer, perfluoroalkoxy (PFA) polymer, fluorinated ethylene propylene (FEP) polymer, TFE-PMVE copolymer, ethylene tetrafluoroethylene (ETFE) polymer, ethylene chlorotrifluoroethylene (ECTFE) polymer, polyvinylidene fluoride (PVDF) polymer, polyether block amide polymer, such as Pebax®, and combinations thereof. Other materials may also be used for constructing the delivery tube, such as, polyester ether ketone materials, polyetherimide (PEI), a polymer of tetrafluoroethylene, hexafluoropropylene and vinylidene fluoride, or combinations thereof. The delivery tube may also be rendered lubricious with materials and coatings as known in the art, e.g., PTFE, ePTFE, other fluoropolymers, hydrogels, and the like.

In addition, any of the materials used in fabricating the delivery tube may be reinforced to increase longitudinal stiffness, e.g., permit pushability of the delivery tube. Accordingly, the delivery tube may be reinforced with materials such as fibers, wires, coils, braids, and the like as known in the art.

The delivery tube may also include a sheath circumferentially covering at least a portion of the anchoring component and/or substantially the entire delivery tube. Preferably, the sheath has a tapered portion arranged over at least one of the fixing components, thereby contouring with the delivery tube. The sheath may be constructed from similar materials to the delivery tube as described herein. Preferably, the sheath is formed from polyether block amide polymer such as Pebax®.

A coupling unit may be used with the medical apparatus and medical scope to detachably couple the medical scope and the apparatus. In one embodiment, the coupling unit and medical apparatus may be configured in a side-by-side arrangement. The coupling unit may be formed from a flexible and/or distensible material arranged over at least a portion of the medical scope to detachably couple the medical scope to the apparatus. The flexible material and/or distensible material may be a thermoplastic material such as a fluoropolymer, e.g., expanded polytetrafluoroethylene (ePTFE), polytetrafluoroethylene (PTFE), and the like. Of course, other materials may also be used for constructing the coupling unit as known in the art.

The coupling unit material may be formed to include at least open regions for receiving the medical scope and apparatus. For example, the coupling unit may be configured as a sock-like apparatus having at least two passageways for receiving the medical scope and the delivery tube. Of course, the coupling unit may also include multiple passages for receiving additional instruments such as tools and the like. The material may also be reinforced with composites, fibers, wires, coils, braids, and the like as known in the art.

The sleeve is a conduit for transporting ingested materials, e.g., pre-digested food, chyme, gastrointestinal material and fluid found in the stomach, and the like. The sleeve is designed to permit at least partial isolation of ingested material and/or gastrointestinal juices, such as, bile and pancreatic juices, from at least portions of the gastrointestinal tract. For example, the sleeve may permit at least partial isolation of chyme from at least portions of villi in the gastrointestinal tract. Preferably, the sleeve is at least a partially compressible conduit that does not substantially inhibit peristaltic mechanisms of the gastrointestinal tract and/or other mechanisms of transport, thereby permitting transport of ingested materials throughout the conduit.

The sleeve may be partially or fully inverted and contained within the lumen of the delivery tube. Preferably, the sleeve is substantially fully inverted and is contained within at least a portion of the delivery tube's lumen. Alternatively, the sleeve may be substantially fully everted over a portion of the delivery tube. Everted is defined as at least a portion of the sleeve is turned inside out, that is, an inside surface of the sleeve is turned to be an outside surface of the sleeve.

The sleeve may include markings to allow a physician to determine the appropriate deployment, e.g., orientation, location, etc., of the sleeve or alternatively to allow tailoring the sleeve to the desired length. The markings may also include a radiopaque material to aid in non-invasive visualization or other suitable visualization materials as known in the art. For example, the sleeve may have at least one longitudinal strip of radiopaque material incorporated into at least a portion of the sleeve's length.

A physician may tailor the sleeve into any length suitable for treatment of obesity and/or diabetes as determined necessary. For example, the sleeve may have a length ranging from about 2 cm to 1000 cm. Preferably, the length of the sleeve ranges from about 50 cm to 200 cm.

The sleeve may be designed to have any number of different geometrically shaped cross-sections, such as circular, oval, elliptical, diamond, square, combinations thereof and the like. In addition, the sleeve may narrow along its length, e.g., having a tapered shape. For example, a cross-section at on location of sleeve may be larger than a cross-section at another of the sleeve. Preferably, the sleeve is designed to have a circular cross-section. In addition, the sleeve may include localized regions of restricted or enlarged cross-sections.

The outside dimension of the sleeve is preferably sized to permit the sleeve to fit within a patient's internal gastrointestinal tract. The outside dimension of the sleeve may also be oversized or undersized within a patient's gastrointestinal tract, that is, the outermost dimension, e.g., the outside diameter may be greater or less than the diameter of the gastrointestinal tract. Preferably, when utilizing a circular cross-section the outside diameter may be in the range from about 15 mm to about 50 mm, and more preferably, the outside diameter ranges from about 20 mm to 30 mm.

The sleeve is preferably sized to permit peristaltic mechanisms of the gastrointestinal tract and/or other mechanisms of transport down the length of the sleeve. The thickness is chosen to permit transport of ingested materials throughout the conduit via peristaltic or other mechanisms. Preferably, the thickness of the sleeve ranges from about 0.003 mm to about 2.6 mm, and more preferably, it ranges from about 0.02 mm to about 0.7 mm thick. The thickness of the sleeve may also vary along the length of the sleeve, for example, the sleeve may be thicker at one end and thinner at an opposite end.

Multiple manufacturing techniques may be used to form the sleeve as known in the art. For example, these techniques can take the form of an extruded or otherwise formed sleeve of a composition that provides mechanical and physical properties that allow at least partial isolation of material exiting the stomach from the small intestine. For example, the sleeve provides at least partial isolation of ingested materials within the sleeve from the digestive tract environment. This isolation may be complete, incomplete, and may vary over time the sleeve is in the patient, vary down the length of the sleeve, and combinations of the same. Preferably, the isolation is designed to provide at least partially impaired absorption of nutrients down a portion of the small intestine, thereby promoting weight loss in the patient.

The sleeve can be constructed, in whole or in part, utilizing a variety of degradable materials, polymeric materials, synthetic or natural, and combinations thereof. In some embodiments, the sleeve may be composed of multiple components that are mixed as a blend, such as a plasticized system, and/or as a microphase immiscible system. If suitable reactive groups are introduced into the formed sleeve, what is commonly known as a thermoset or chemically cross-linked system can be generated under appropriate curing conditions. The formed sleeve can also be composed in the form of a laminate or a fibrous reinforced composite. Of course, the properties of the selected composition, e.g., molecular weight, glass transition temperature(s), crystallinity, and/or the extent of cross-linking will dictate the desired properties of the sleeve. The sleeve may also be coated with a variety of therapeutic agents such as vitamin coatings, drug coatings, and the like. The vitamin coatings may be designed to mimic or supplement therapeutic vitamin therapies implemented to patients of traditional weight loss therapies.

Degradable materials include bioabsorbable materials and biodigestible materials as discussed herein. Biodigestible includes a material that is capable of being converted into assimilable condition in the alimentary canal or capable of being at least partially decayed to allow passing of the material. Bioabsorbable materials include bioabsorbable polymers and copolymers composed from varying amounts of one or more of the following monomer examples, glycolide, d,l-lactide, l-lactide, d-lactide, p-dioxanone (1,4-dioxane-2-one), trimethylene carbonate (1,3-dioxane-2-one), ε-caprolactone, γ-butyrolactone, δ-valerolactone, 1,4-dioxepan-2-one, and 1,5-dioxepan-2-one. Polymers that are either introduced as or can be degraded to segment lengths that can be excreted from the body can also be considered as bioabsorbable, and may include polyethylene glycol, polypropylene glycol, amino acids, anhydrides, orthoesters, phosphazines, amides, urethanes, and phosphoesters. Alternative copolymers may possess, in whole or in part, block, segmented, random, alternating, or statistical polymeric construction characteristics. Animal derived products such as elastin or collagen, either absorbable, e.g., enzymatically degraded, within the body or rendered non-absorbable through chemical treatment, e.g., glutaraldehyde cross-linked bovine pericardium, may alternatively be utilized as or within the sleeve construct. Additional potential components of the sleeve may include naturally derived or modified polysaccharides such as chitosan, alginate, and/or hyaluronic acid.

In a preferred embodiment, the sleeve is constructed from a composite of ePTFE and FEP materials. The composite has FEP layer on one side of the laminate and ePTFE on the opposite side. The composite film possessed the following properties: a thickness ranging from about 0.002 mm to about 0.7 mm, and more preferably, it ranges from about 0.02 mm to about 0.3 mm thick. An IPA bubble point of greater than about 0.6 MPa, and a tensile strength of at least about 75 MPa in the weakest direction. More preferably, also having a tensile strength of about 309 MPa in the strongest direction. In a preferred embodiment, the resultant sleeve is impermeable to gastrointestinal fluids, e.g., chyme, biliopancreatic fluids, digested foods, stomach acids and the like.

The sleeve may be fabricated in a continuous or batch process as known in the art. In one embodiment, a plurality of film strips may be arranged in the longitudinal direction along the length of a mandrel. The strips may be evenly or non-evenly spaced along the length of mandrel, that is, the strips may overlap or not overlap with each other. In a preferred embodiment, the strips are a composite film of FEP and ePTFE, however, other sleeve materials as described herein may be utilized. In this embodiment, the FEP side of the film may be arranged such that it is up or away from the mandrel.

The mandrel with the longitudinal oriented film may then be helically wrapped with another composite film. The helically wrapped film may be the same or different type material as the previously used composite film. The FEP may be oriented down towards the mandrel and against the longitudinal film. A helical wrapper may be used to apply the film at a predetermined pitch. Pitch is defined as the amount of advance per revolution of the mandrel. The longitudinal and helical wrapping processes may be repeated one or more times.

The film layered mandrel may then be placed into an oven, e.g., air convection oven set to a temperature ranging from about 250 to 400° C., and more preferably to a temperature ranging from about 300 to 340° C. It may be heated in the oven for time ranging from about 15 to 60 minutes, and more preferably for a time ranging from about 25 to 35 minutes. Upon removal from the oven the resultant sleeve is cooled to room temperature. Alternatively, other suitable techniques as known in the art may be utilized in fabrication of the sleeve.

Next, the sleeve may be attached to the anchoring component with a coupling agent. The coupling agent may include a starch, cyanoacrylates, silicone, urethane, and/or thermoplastics, e.g., fluoropolymers, nylon, perfluoroalkoxy (PFA), polyurethane (PU), fluorinated ethylene propylene (FEP), and others as known in the art. Preferably, the coupling agent has acceptable biocompatibility and is formed from copolymers, such as a tetrafluoroethylene perfluoroalkylvinylether copolymer (TFE/PAVE), a tetrafluoroethylene perfluoromethylvinylether copolymer (TFE/PMVE), and combinations thereof. Of course, bioabsorbable materials may also be used such as polyglycolic acid and trimethylene carbonate monomer (PGA/TMC), polyglycolic acid and polylactic acid (PGA/PLA), and combinations thereof.

The anchoring component may be a self-expandable, balloon-expandable or a combination of self-expandable and balloon-expandable anchoring components. In some embodiments, the anchoring component is used to at least partially fix the device inside a portion of the gastrointestinal tract, e.g., before, across, or after the pylorus. Other anchoring locations are also possible, for example it may be arranged in the esophagus; at the gastroesophageal interface; and/or in the small intestine. For example, the anchoring component may be arranged prior to the pylorus, in the stomach antrum, across the pylorus, in the duodenum bulb, in the small intestine or at another suitable site.

The anchoring component is preferably constructed from materials that are flexible and strong. The anchoring component may be formed from degradable bioabsorbable materials, biodigestible materials, polymeric materials, metallic materials and combinations thereof. In addition, these materials may be reinforced and/or coated with other materials, such as polymeric materials and the like. The coating may be chosen to reduce acidic or basic effects of the gastrointestinal tract, e.g., with a thermoplastic coating such as ePTFE and the like.

The anchoring component may be formed into a variety of different geometric configurations having constant and/or varied thickness as known in the art. The geometric configurations may include many conventional stent configurations such as a helical wrapped stent, z-shape stent, tapered stent, coil stent, combinations and the like. Moreover, the anchoring component may be designed to have a flange on one side and a coil shape on the opposite side. Preferably, the anchoring component has a tapered configuration, that is, where one end of the component has a larger dimension than the opposite end. This tapered configuration is thought to provide better anchoring proximally or distally to the pylorus.

The anchoring component may be designed to degrade or decompose over time. For example, the anchoring component may be designed to degrade with exposure to the acidic or basic environment of the anatomy. In these configurations, the anchoring component may be constructed from biodigestible materials and/or bioabsorbable materials. Biodigestible materials include acidic or basic degradable metals and alloys, such as, iron, aluminum, chromalloy, and the like. Of course, other materials that degrade over time as known in the art may also be utilized in the fabrication of the anchoring component.

By way of example, bioabsorbable self-expanding anchoring components may be manufactured as taught in U.S. Patent Application Publication 2006/0025852. For example, an integral framework in a substantially tubular shape can be utilized. The integral framework elements include bioabsorbable materials such as these described herein. In one embodiment, the materials include non-blended hydrolysable polymer material in a tri-block co-polymer of poly(glycolide) and poly(trimethylenecarbonate).

In another embodiment, the anchoring component is constructed from a super-elastic material such as nitinol. The material may be formed from a cut tube material or wire material. The material is sized to have a thickness ranging from about 0.01 to 0.5 mm or more. The material may have any cross-sectional geometry, e.g., a circle, oval, square, triangle, ribbon and the like.

The anchoring component may be manufactured as known in the art, e.g., laser cutting a tube. In one embodiment, the anchoring component is formed from a wire, e.g., nitinol wire. The wire is arranged around variously spaced pins on a jig. The pins are spaced on the jig into a desired geometric pattern. The pins act to hold the wire in a desired shape during a subsequent thermal setting process. In addition, the jig may be tapered or straight along a longitudinal axis. Preferably, the jig is constructed from a stainless steel cylinder. The wire is wrapped around the various pins to form the anchoring component. Each end of the wire is terminated under a termination unit, e.g., screw head that hold an end of the wire.

The wire and jig are placed into a heat source, e.g., a convection oven, at a shape setting temperature. Preferably, when utilizing super-elastic nitinol wire the shape setting temperature ranges from about 440° C. to 500° C., and more preferably from about 460° C. to 480° C. The super-elastic nitinol wire is placed into the heat source for time ranging from about 10 to 40 minutes, and more preferably for time from about 15 to 20 minutes. Upon removal, the jig and wire are submersed in a water bath at room temperature. After the jig has cooled and dried the anchor component is removed and any excess wire may be trimmed.

Reference will now be made in detail to various embodiments of the invention, examples of which are illustrated in the accompanying drawings.

Figure 1B:
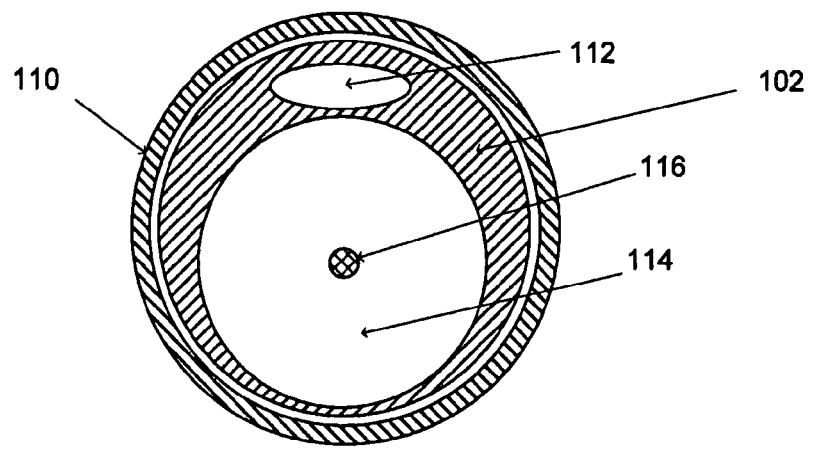
FIG. 1B illustrates a cross-sectional end view of the apparatus shown in FIG. 1A cut along line I to I'.

FIG. 1A illustrates a cross-sectional view of a medical apparatus according to an embodiment of the invention. FIG. 1B illustrates a cross-sectional end view of the apparatus shown in FIG. 1A cut along line I to I'.

Referring to FIGS. 1A and 1B, the medical apparatus is generally depicted as reference number 100. The apparatus 100 includes a delivery tube 102 having fixing components 104. The fixing components 104 are used to prevent the anchoring component 106 from substantially moving along the axis of the delivery tube 102.

Optionally, a balloon 108 may be positioned beneath at least a portion of the anchoring component 106. The balloon 108 may be used to assist in the placement of the anchoring component 106 and/or expansion of the anchoring component 106. When a balloon 108 is used, the delivery tube 102 has an additional inflation port for inflating the balloon 108 as known in the art, for example, the delivery tube 102 may have an internal lumen with an inflation port under at least a portion of the balloon 108.

In this embodiment, the delivery tube 102 is configured to fit within a working channel of an endoscope (not shown), thereby having a diameter ranging from about 10 mm or less. Alternatively, the delivery tube 102 may be configured to fit within a coupling unit (not shown) in a side-by-side arrangement with the endoscope. The delivery tube 102 also includes a sheath 110 circumferentially covering at least a portion of the anchoring component 106 and/or substantially the entire delivery tube 102. Preferably, the sheath 110 has an enlarged portion 111. The enlarged portion 111 is arranged over at least a portion of the anchoring component 106. The sheath 110 also may overhang a distal portion 117 of the delivery tube 102. That is, the sheath may extend about 2 to 4 mm or more past a distal end of the delivery tube 102. The sheath 110 may be constructed from similar materials to the delivery tube 102 as described herein. Preferably, the sheath 110 is formed from polyether block amide material, such as Pebax® material.

The delivery tube 102 may also include a connector 119 that is coupled to a proximal end 121 of the delivery tube 102. The connector 119 is designed to permit a detachable connection to a syringe or other medical pressurization source that may be utilized in the everting process of the sleeve 116. The connector 119 may be configured to be in fluid communication with one or both lumens of the delivery tube 102 as known in the art. For example, the connector may be configured to be in fluid communication with only the inflation port 112 used in the deployment of the sleeve 116. In addition, the sheath 110 may also include a hub 115 near a proximal end of the delivery tube 102. The hub may include an ergonomic handle allowing medical personnel better hand placement to retract the sheath 110 during deployment, e.g., to slide the sheath axially along the delivery tube 102.

As shown in FIG. 1B, the delivery tube 102 has two lumens extending from a proximal end to a distal end. In this embodiment, the first lumen 112 is configured to be used as an inflation port during the deployment of the sleeve 116. The first lumen 112 has a substantially oval shape. At least a portion of the sleeve 116 is arranged within a portion of the second lumen 114. The second lumen 114 is arranged in a substantially circular configuration. However, as discussed herein, other geometric shapes for either the first lumen 112 or the second lumen 114 are possible and part of this invention. The sleeve 116 is substantially fully inverted inside a portion of the second lumen 114. Preferably, the sleeve is also radially compressed with a compression apparatus.

Figure 2:
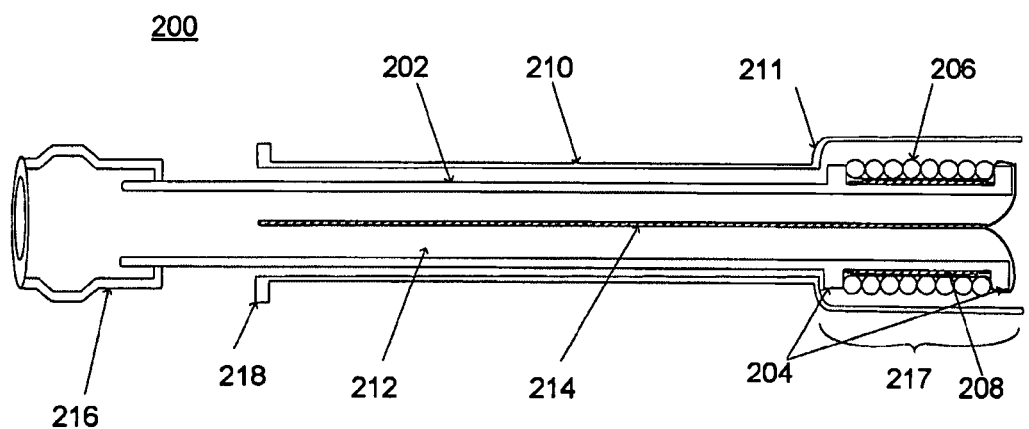
FIG. 2 illustrates a cross-sectional view of a medical apparatus according to another embodiment of the invention.

FIG. 2 illustrates a cross-sectional view of a medical apparatus according to another embodiment of the invention.

Referring to FIG. 2, the medical apparatus is generally depicted as reference number 200. The apparatus 200 includes a delivery tube 202 having fixing components 204. The fixing components 204 are used to prevent the anchoring component 206 from substantially moving along the axis of the delivery tube 202. Alternatively, the anchoring component 206 may be arranged on an inside portion of the delivery tube 202.

Optionally, a balloon 208 may be positioned beneath at least a portion of the anchoring component 206. The balloon 208 may be used to assist in the placement of the anchoring component 206 and/or expansion of the anchoring component 206. When a balloon 208 is used, the delivery tube 202 has an additional inflation port for inflating the balloon 208 as known in the art. For example, the delivery tube 202 may have an internal lumen with an inflation port under at least a portion of the balloon 208.

In this embodiment, the delivery tube 202 is configured to fit within a working channel of an endoscope (not shown), thereby having a diameter ranging from about 10 mm or less. Alternatively, the delivery tube 202 may be configured to fit within a coupling unit (not shown) in a side-by-side arrangement with the endoscope. A sheath 210 circumferentially covers at least a portion of the anchoring component 206 and/or substantially the entire delivery tube 202. Preferably, the sheath 210 has an enlarged portion 211. The enlarged portion 211 is arranged over at least a portion of the anchoring component 206. The sheath 210 also may overhang the distal portion 217 of the delivery tube 202. That is, the sheath 210 may extend about 2 to 4 mm or more past a distal end of the delivery tube 202. The sheath 210 may be constructed from similar materials to the delivery tube 102 as described herein. Preferably, the sheath 110 is formed from polyether block amide material, such as Pebax® material.

In this embodiment, the delivery tube 202 has only one lumen 212 extending throughout the tube, i.e., from a proximal end to a distal end. The sleeve 214 is substantially fully inverted and arranged within the lumen 212 of the delivery tube 202. The sleeve 214 is optionally radially compressed prior to inserting into the lumen of the delivery tube 202. The lumen 212 is also used as an inflation port for everting the sleeve 214 into the desired location.

The delivery tube 202 may also include a connector 216 coupled to a proximal end of the delivery tube 202. The connector 216 is designed to permit a detachable connection to a pressurization source, e.g., a syringe or other device, that may be utilized in the everting process of the sleeve 214. The connector 216 is configured to be in fluid communication with the lumen 212. In addition, the sheath 210 may also include a hub 218 near a proximal end of the sheath 210. The hub 218 may include an ergonomic handle (not shown), allowing a medical personnel better hand placement to retract the sheath 210 during deployment, e.g., to slide the sheath axially along the delivery tube 202.

Figure 3:
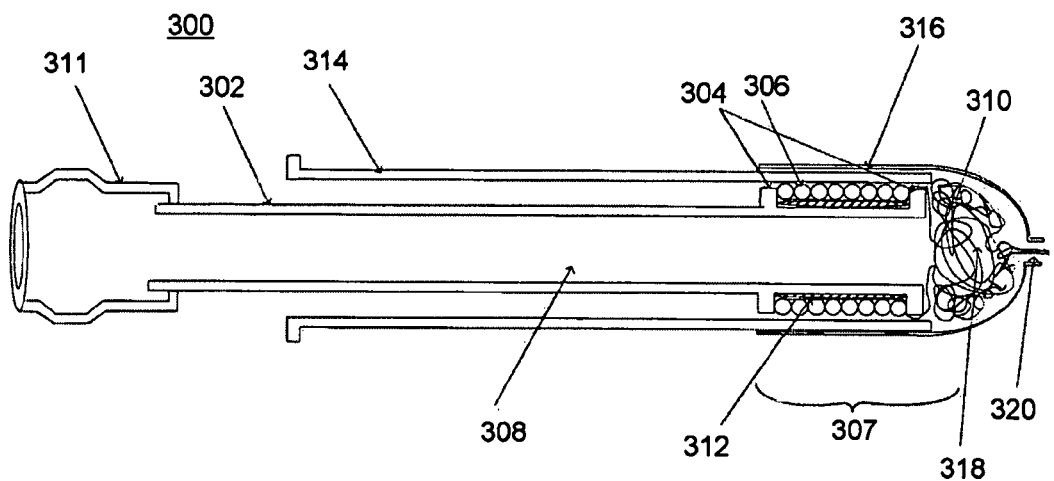
FIG. 3 illustrates a cross-sectional view of a medical apparatus according to another embodiment of the invention.

FIG. 3 illustrates a cross-sectional view of a medical apparatus according to another embodiment of the invention.

Referring to FIG. 3, the medical apparatus is generally depicted as reference number 300. The apparatus 300 includes a delivery tube 302 having fixing components 304 arranged near a distal end portion 307 of the delivery tube 302. The fixing components 304 are used to prevent the anchoring component 306 from substantially moving along an axis of the delivery tube 302. The delivery tube 302 includes at least one lumen 308 that may be used as an inflation port in deploying the sleeve 310. The delivery tube 302 may be configured to fit within a working channel of a medical scope (not shown). A connector 311 is arranged on a portion of the delivery tube and is configured to be in fluid communication with the lumen 308.

Optionally, a balloon 312 may be positioned beneath at least a portion of the anchoring component 306. The balloon 312 may be used to assist in the placement of the anchoring component 306 and/or expansion of the anchoring component 306. When a balloon 312 is used the delivery tube 302 has an additional inflation port for inflating the balloon 312 as known in the art. For example, the delivery tube 302 may have an internal lumen with an inflation port under at least a portion of the balloon 312.

A sheath 314 circumferentially covers the delivery tube 302. A cap 316 is arranged over at least a distal portion 307 of the delivery tube 302. Alternatively, the cap 316 may be arranged over or under a portion of the sheath 314. There is a space 318 created between the distal end of the delivery tube 302 and the inner surface of the cap 316. The sleeve 310 is at least partially arranged within the space 318 and/or inverted inside a portion of the lumen 308.

The cap 316 optionally includes an aperture 320 where a portion of the sleeve 310 may extend outside the aperture 320, thereby allowing adjustment of the sleeve 310 length prior to deploying the sleeve 310. That is, the sleeve 310 may be adjusted by removing, e.g., cutting, a predetermined portion of the sleeve 310 to the desired therapeutic length by pulling at least a portion of the sleeve 310 to be cut outside the aperture 320. The cutting of the sleeve 310 may be accomplished prior to insertion of the apparatus 300 into the patient.

Figure 4A:
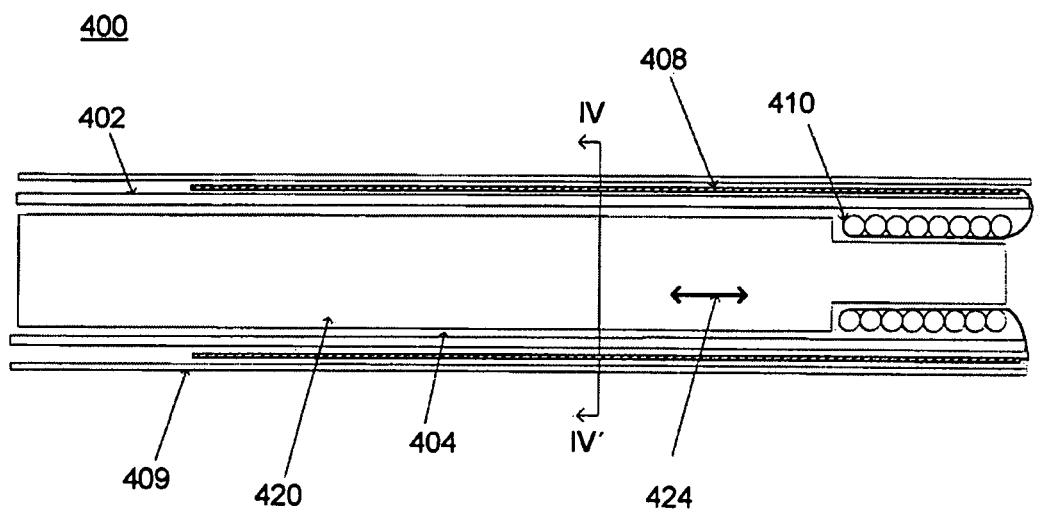
FIG. 4A illustrates a cross-sectional view of a medical apparatus according to another embodiment of the invention.
Figure 4B:
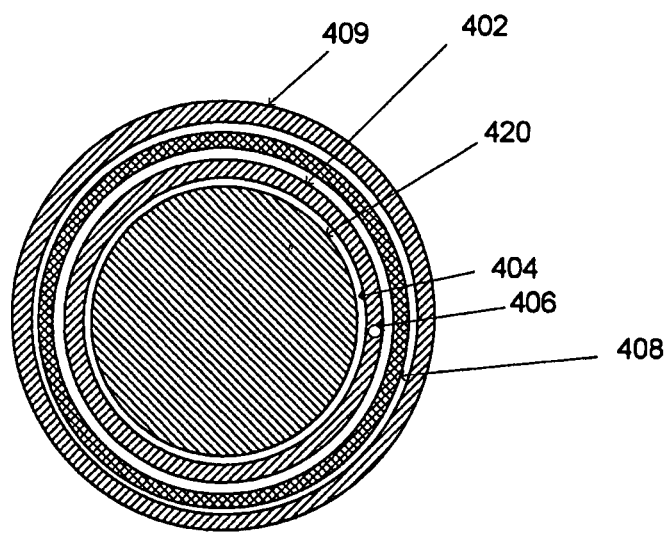
FIG. 4B illustrates a cross-sectional end view of FIG. 4A cut along line IV to IV'.

FIG. 4A illustrates a cross-sectional view of a medical apparatus according to another embodiment of the invention. FIG. 4B illustrates a cross-sectional end view of FIG. 4A cut along line IV to IV'.

Referring to FIGS. 4A and 4B, the medical apparatus is generally depicted as reference number 400. The apparatus 400 includes a delivery tube 402 having a first lumen 404 and a second lumen 406 extending from a proximal end to a distal end of the delivery tube 402. More specifically, the second lumen 406 extends throughout a wall of the delivery tube as shown in FIG. 4B and may be used for deploying a sleeve 408. Of course, additional lumens may also be utilized. The sleeve 408 is attached to a portion of the anchoring component 410 and everted over at least a portion of the delivery tube 402. A sheath 409 is arranged over at least a portion of the everted sleeve 408. The delivery tube 402 may be configured to fit within a working channel of an endoscope (not shown) or it may be configured to fit within a coupling unit (not shown) in a side-by-side arrangement with the endoscope.

A pushrod 420 is arranged within the delivery tube 402 to allow at least lateral movement of the pushrod 420 as indicated by arrow 424. The pushrod 420 may be hollow or solid. The pushrod 420 is used in the deployment of the anchoring component 410. For example, the pushrod 420 may be moved to deploy the anchoring component 410 out the distal end of the delivery tube 402.

Figure 5A:
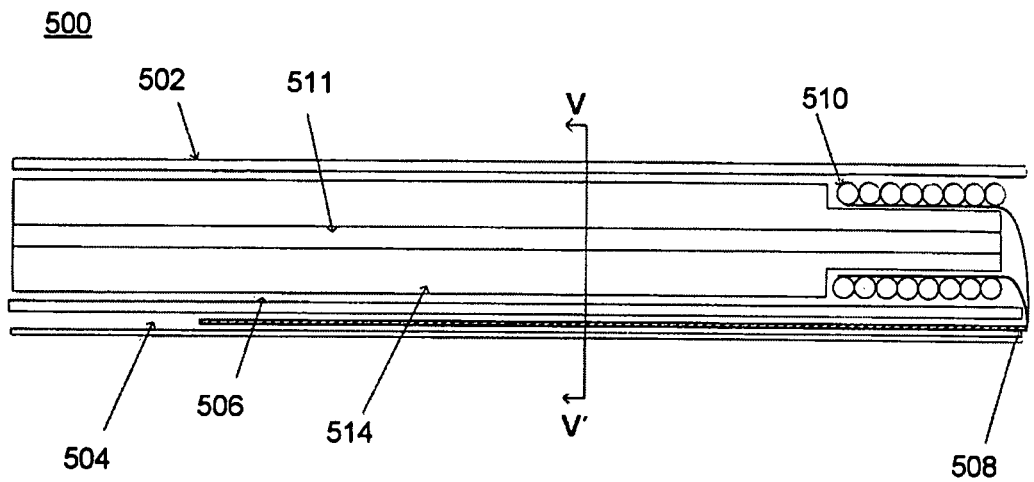
FIG. 5A illustrates a cross-sectional view of a medical apparatus according to another embodiment of the invention.
Figure 5B:
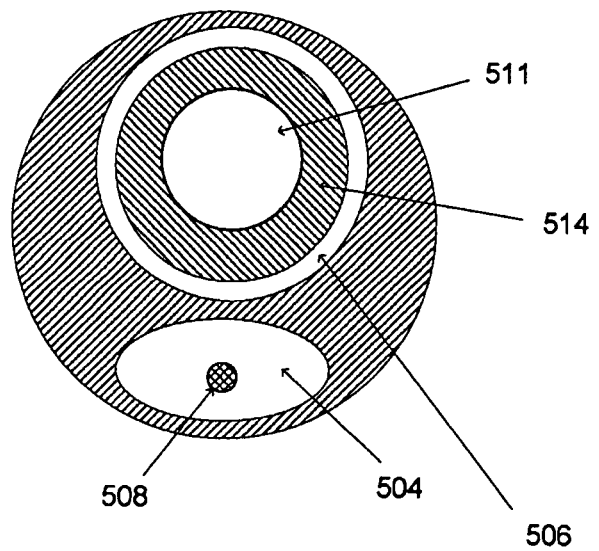
FIG. 5B illustrates a cross-sectional end view of FIG. 5A cut along line V to V'.

FIG. 5A illustrates a cross-sectional view of a medical apparatus according to another embodiment of the invention. FIG. 5B illustrates a cross-sectional end view FIG. 5A cut along line V to V'.

Referring to FIGS. 5A and 5B, the medical apparatus is generally depicted as reference number 500. The apparatus 500 includes a delivery tube 502 having a first lumen 504 and a second lumen 506. Either the first 504 or second 506 lumen can be used for holding a portion of an inverted sleeve 508. Preferably, at least a portion of the sleeve 508 is radially compressed to reduce its profile. The sleeve 508 is attached to at least a portion of the anchoring component 510. The delivery tube 502 may be configured to fit within a working channel of an endoscope (not shown) or configured to fit within a coupling unit (not shown) in a side-by-side arrangement with the endoscope. The delivery tube 502 may include a connector (not shown) at the proximal end as described herein.

A pushrod 514 is arranged within a lumen of the delivery tube to allow at least lateral movement of the pushrod 514. The pushrod 514 may be hollow or solid and is used in the deployment of the anchoring component 510 out an end of the delivery tube 502. In the embodiment, the pushrod 514 includes an inflation port 511 that may be used for deploying the sleeve 508.

Figure 6A:
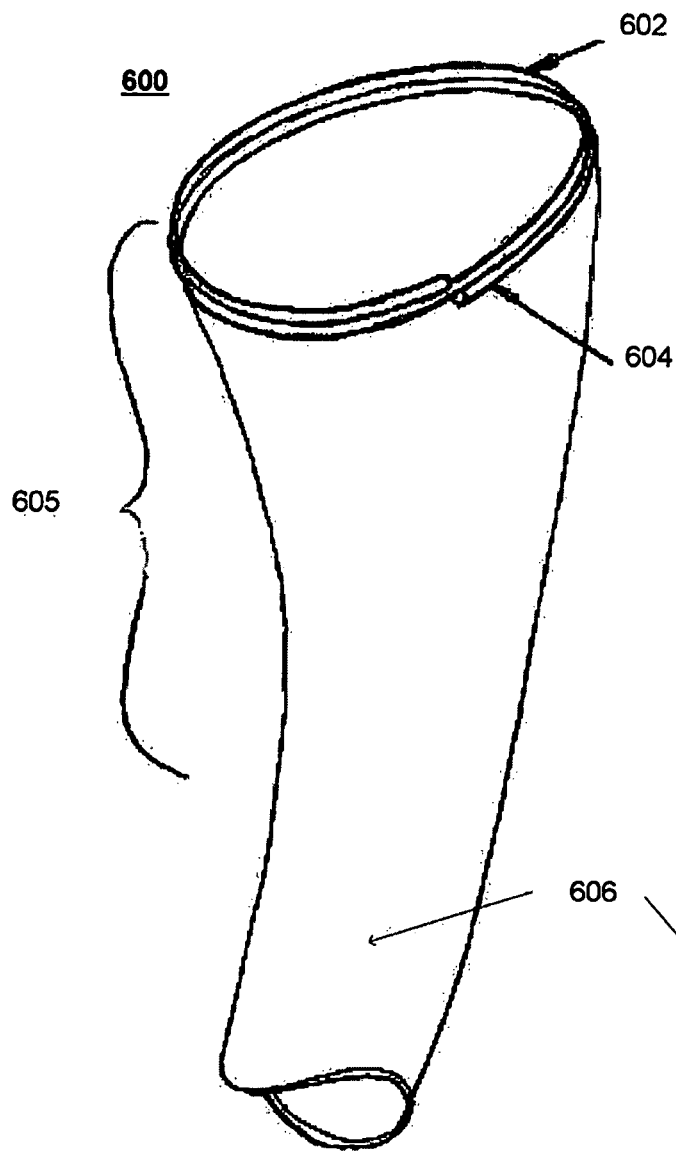
FIG. 6A illustrates an anchoring component according to an embodiment of the invention.
Figure 6B:
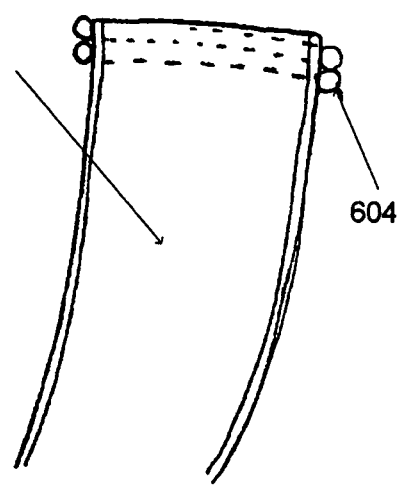
FIG. 6B illustrates an cross-sectional view of FIG. 6A.
Figure 6C:
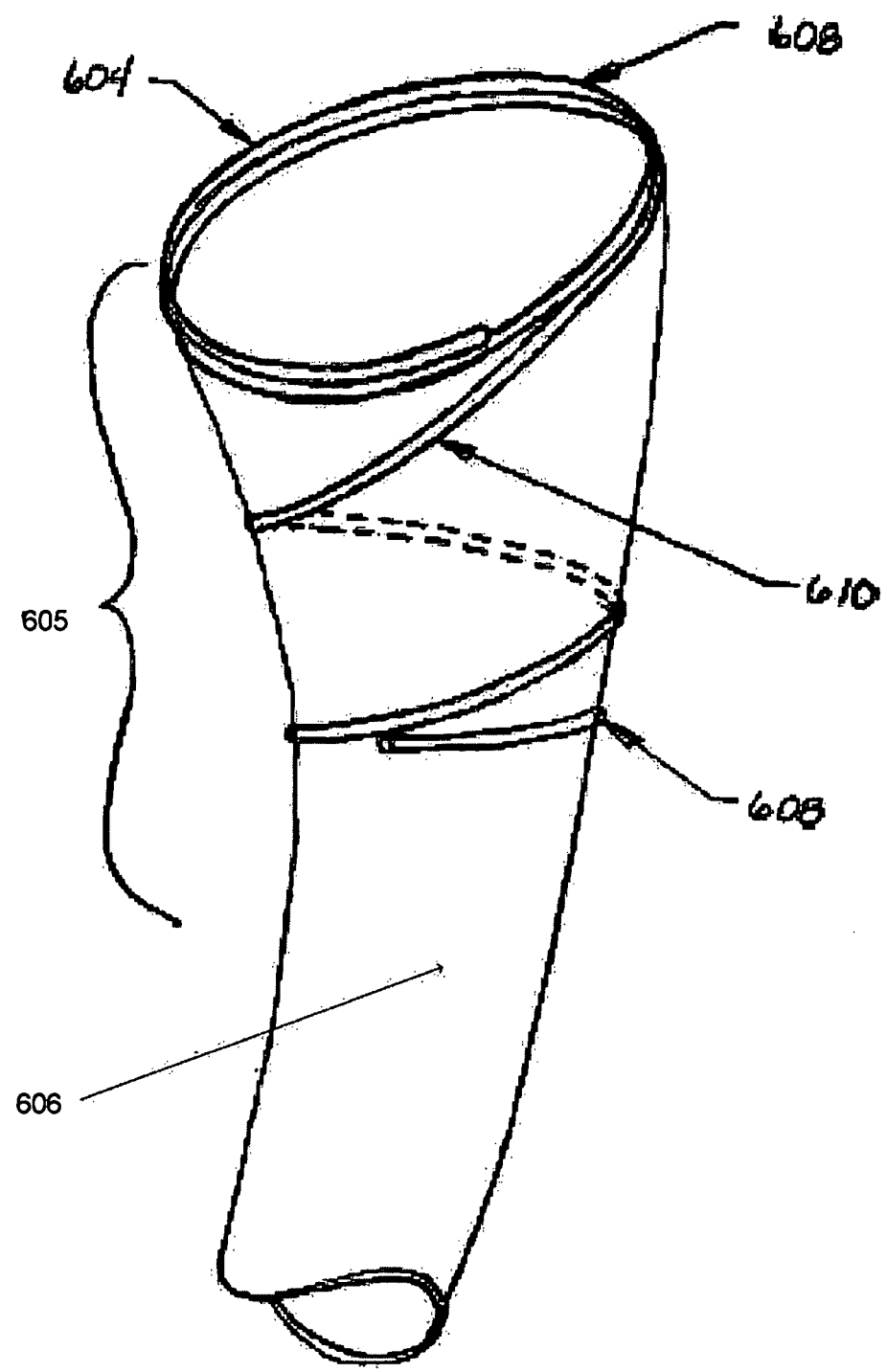
FIG. 6C illustrates an anchoring component according to another embodiment of the invention.
Figure 6D:
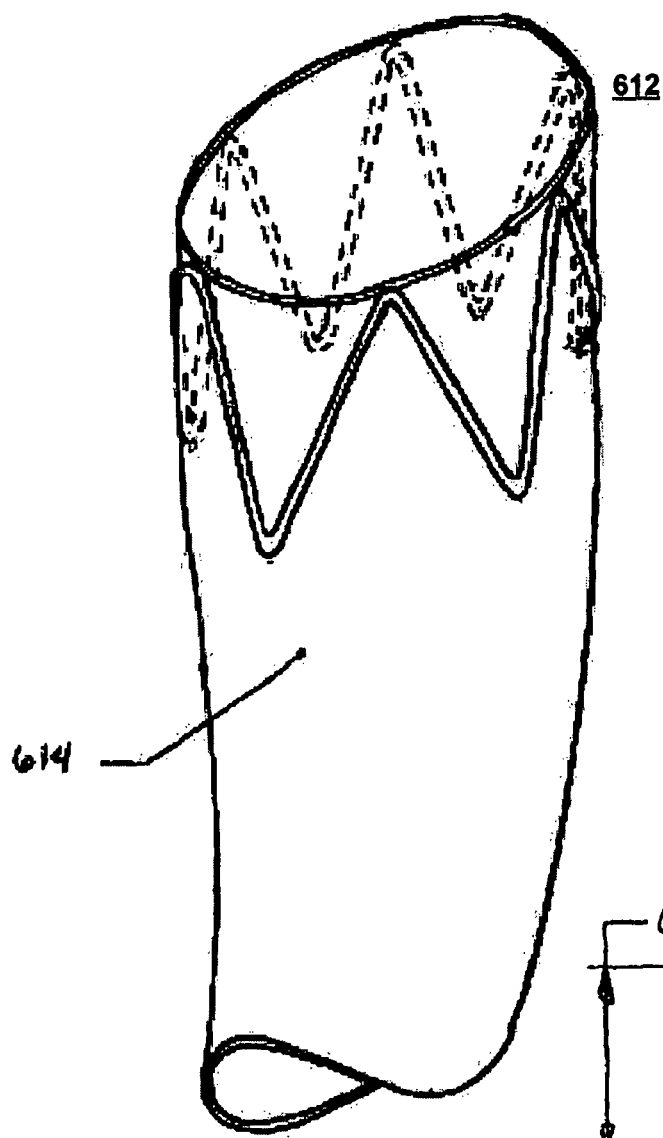
FIG. 6D illustrates an anchoring component according to another embodiment of the invention.
Figure 6E:
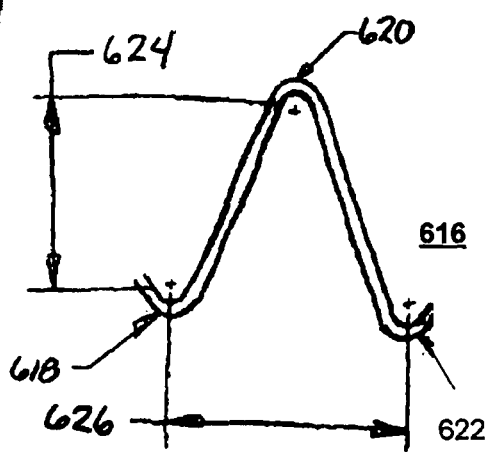
FIG. 6E illustrates an enlarged section view of a portion of the anchoring component shown in FIG. 6D.

FIGS. 6A-6K illustrate various anchoring components according to various embodiments of the invention. FIG. 6L illustrates active and passive anchoring elements according to an embodiment of the invention.

Referring to FIGS. 6A-6L, the anchoring components may be used individually by being attached anywhere along the sleeve, for example, by being attached a near a distal end or proximal end of the sleeve. In addition, the anchoring components may also be used as module components with each other, that is, more than one anchoring component may be used with the sleeve.

Figure 6F:
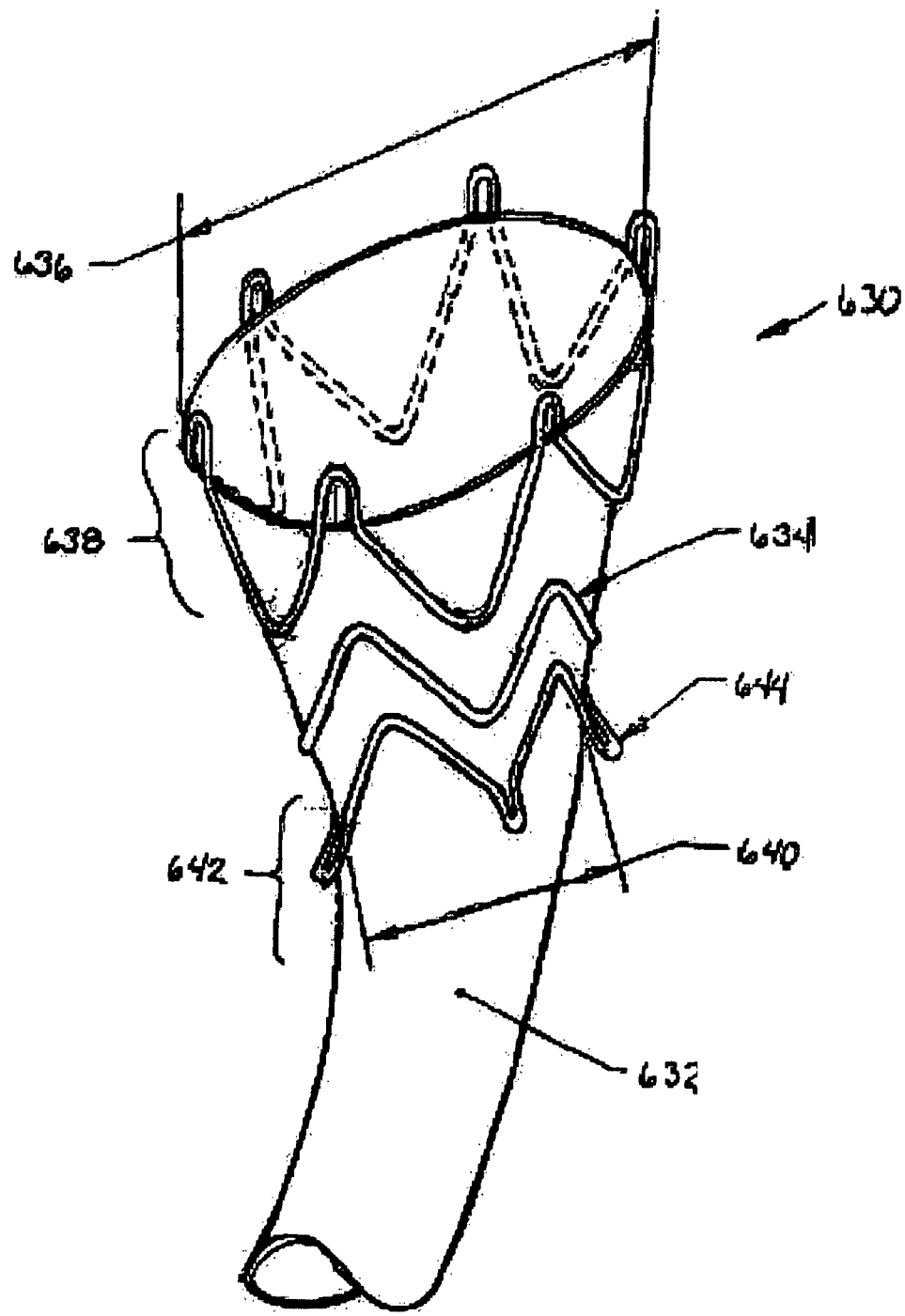
FIG. 6F illustrates an anchoring component according to another embodiment of the invention.
Figure 7:
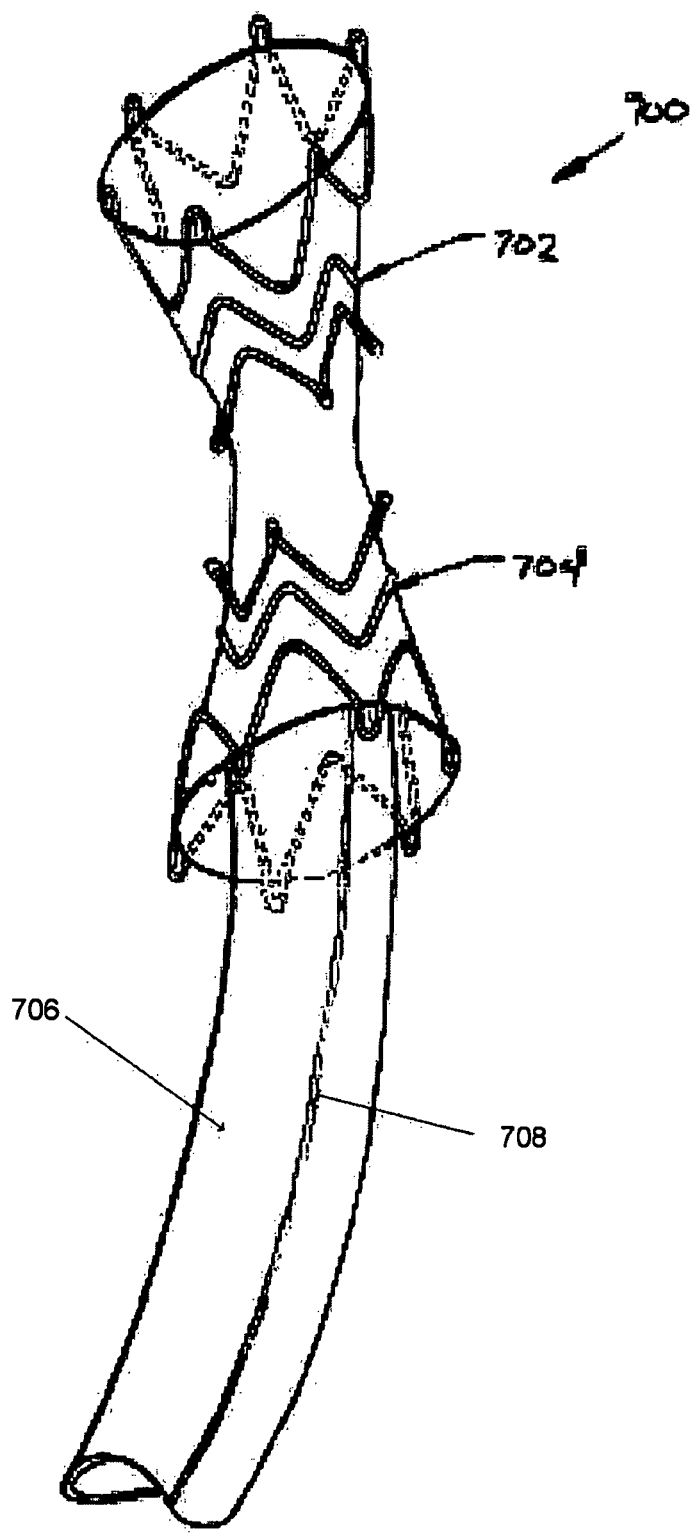
FIG. 7 illustrates a medical device according to another embodiment of the invention.

By way of example, referring to FIG. 7, the anchoring component of FIG. 6F is used in combination with itself. That is, the component of FIG. 6F is used at a first location 702 of the sleeve 706 and the same component of FIG. 6F is positioned in an mirrored configuration at a second location 704. In this configuration, the anchoring component at the first location 702 may be arranged on one side of the pylorus while the mirrored anchoring component at the second location 704 may be arranged within or on an opposite side of the pylorus. Of course, other anchoring component configurations or single anchoring components may be used.

As previously explained herein, the anchoring components may be a self-expandable, balloon-expandable or a combination of self-expandable and balloon-expandable anchoring components. In some embodiments, the anchoring component is used to at least partially fix the device inside a portion of the gastrointestinal tract, e.g., before, across, or after the pylorus. Other anchoring locations are also possible, for example it may be arranged in the esophagus; at the gastroesophageal interface; in the small intestine; in the stomach. For example, the anchoring component may be arranged in the pylorus, in the stomach antrum, across the pylorus, in the duodenum bulb, in the small intestine or at another suitable site.

As previously discussed, the anchoring component is preferably constructed from materials that are flexible and strong. The anchoring component may be formed from degradable bioabsorbable materials, biodigestible materials, polymeric materials, metallic materials and/or combinations thereof. In addition, these materials may be reinforced and/or coated with other materials, such as polymeric materials and the like. The coating may chosen to reduce acidic or basic effects of the gastrointestinal tract, e.g., with a polymeric coating such as ePTFE and the like. The materials may be chosen from known materials in the art. For example, the material may formed from a number of different shapes, e.g., it may be cut from a tube, a wire, a ribbon, and the like.

FIG. 6A illustrates an anchoring component according to an embodiment of the invention. Referring to FIG. 6A, a single ring anchoring component is generally depicted by reference number 600. Multiple or single rings may be used to form a substantially circular ring pattern 602 with a material 604, e.g., wire, which is attached to or near a proximal end 605 of a sleeve 606. In this embodiment, the preferred material is a nitinol wire material, however, the pattern 602 may be formed with a cut tube, a ribbon, and the like as known in the art. The wire has a diameter ranging from about 0.2 to 0.5 mm or more. Now referring to FIG. 6B, the material 604 is wrapped around the sleeve such that it is substantially adjacent to the next wrap of the wire. Of course, the anchoring component will gain in strength, e.g., hoop strength, as the number of wrappings increases. Preferably, there are two to ten or more wrappings of the material 604 around the sleeve 606.

Moreover, the overall pattern 602 does not have to be in a substantially circular pattern as illustrated. That is, the overall pattern may be in any geometric configuration, for example, it may have a substantially oval configuration, substantially rectangular configuration, substantially triangular configuration, substantially octagonal configuration and the like. Preferably, the pattern is a substantially circular pattern having a diameter ranging from about 15 mm to 60 mm or more.

Now referring to FIG. 6C, there may be a plurality of circular patterns 608 separated by a connecting bridge 610 between the patterns 608. The connecting bridge 610 may be constructed to include one or more bends or other means to provide stored-length therein. The bridge 610 can be used to alter the flexural modulus of the anchoring component as well as the degree of endoluminal scaffolding as known in the art. Alternatively, the ring patterns 608 can be independent of one another, that is no connecting bridge 610.

FIG. 6D illustrates an anchoring component according to another embodiment of the invention. FIG. 6E illustrates an exploded view of the anchoring component shown in FIG. 6E.

Referring to FIGS. 6D and 6E, a z-type anchoring component, e.g., z-stent, is generally depicted as reference number 612. The anchoring component 612 is formed in a substantially undulating or zig-zag pattern around the circumference of the sleeve 614. However, other patterns as known in the art may also be used. There includes a plurality of undulating elements 616 with each undulating element including a first apex 618, a second apex 620, and a third apex 622.

Each of the undulating elements 616 includes a height 624 and a width 626. The height is measured vertically from a center radius of an apex 618 to a center radius of an adjacent apex 620. The height range may be dependent upon the size of the anchoring component, e.g., the diameter of the device and the number of apices. Preferably, the height ranges from about 6 to 40 mm or more with a total number of apices ranging from 6 to 18 or more.

FIG. 6F illustrates an anchoring component according to another embodiment of the invention. Referring to FIG. 6F, a helically tapered anchoring component is generally depicted as reference number 630. The helical pitch angle may range from about 2 degrees to 40 degrees. The anchoring component is formed in a substantially undulating or zig-zag pattern around the circumference of the sleeve 632. However, other patterns as known in the art may also be used. The anchoring component includes a plurality of undulating elements 634. Each undulating element 634 includes a first apex, a second apex, and a third apex as previously described with reference to FIG. 6E. In the embodiment, the preferred material is a nitinol wire material, however, the undulating elements may be formed with a cut tube, a ribbon, and the like as known in the art. In this embodiment, the wire has a diameter ranging from about 0.2 to 0.5 mm or more.

Again, each undulating element 634 includes a height and a width. The height range may be dependent upon the size of the anchoring component, e.g., the diameter of the device and the number of apices. The height ranges from about 6 to 40 mm or more with a total number of apices ranging from 6 to 18 or more. The overall geometric configuration of the anchoring component 630 has a tapered geometry with a first diameter 636 ranging from about 40 to about 60 mm or more at a proximal end 638 and a second diameter 640 ranging from about 12 to 30 mm or more at a distal end 642. Preferably, the first diameter 636 ranges from about 36 to 44 mm and the second diameter 640 ranges from about 22 to 30 mm.

More preferably, there are three or more rows of undulating elements circumferentially surrounding the sleeve 632 having progressively smaller diameters, thereby forming a tapered helical pattern. It is appreciated that any pattern enabling circumferential expansion is feasible with the concepts of the invention. Connecting bridges (not shown) may be used between rows of the undulating elements. These bridges may be constructed to include one or more bends or other means to provide stored-length therein. The bridges can be used to alter the flexural modulus of the stent as well as the degree of endoluminal scaffolding as known in the art.

Moreover, anchoring elements 644 may be formed to any portion of the undulating elements. Preferably, the anchoring elements 644 are formed at any undulating element apex. The anchoring elements 644 are preferably designed to promote fixation to a predetermined location. Also, the anchoring elements 644 may be either passive or active as described with reference to FIG. 6L. In this embodiment, the anchoring elements 644 are passive and added to the apices of the undulating elements on the proximal and distal end portions of the anchoring component 630. These anchoring elements 644 are protruding to provide fixation into the desired tissue, thereby substantially fixing the anchoring component 630 from dislodgement.

Figure 6G:
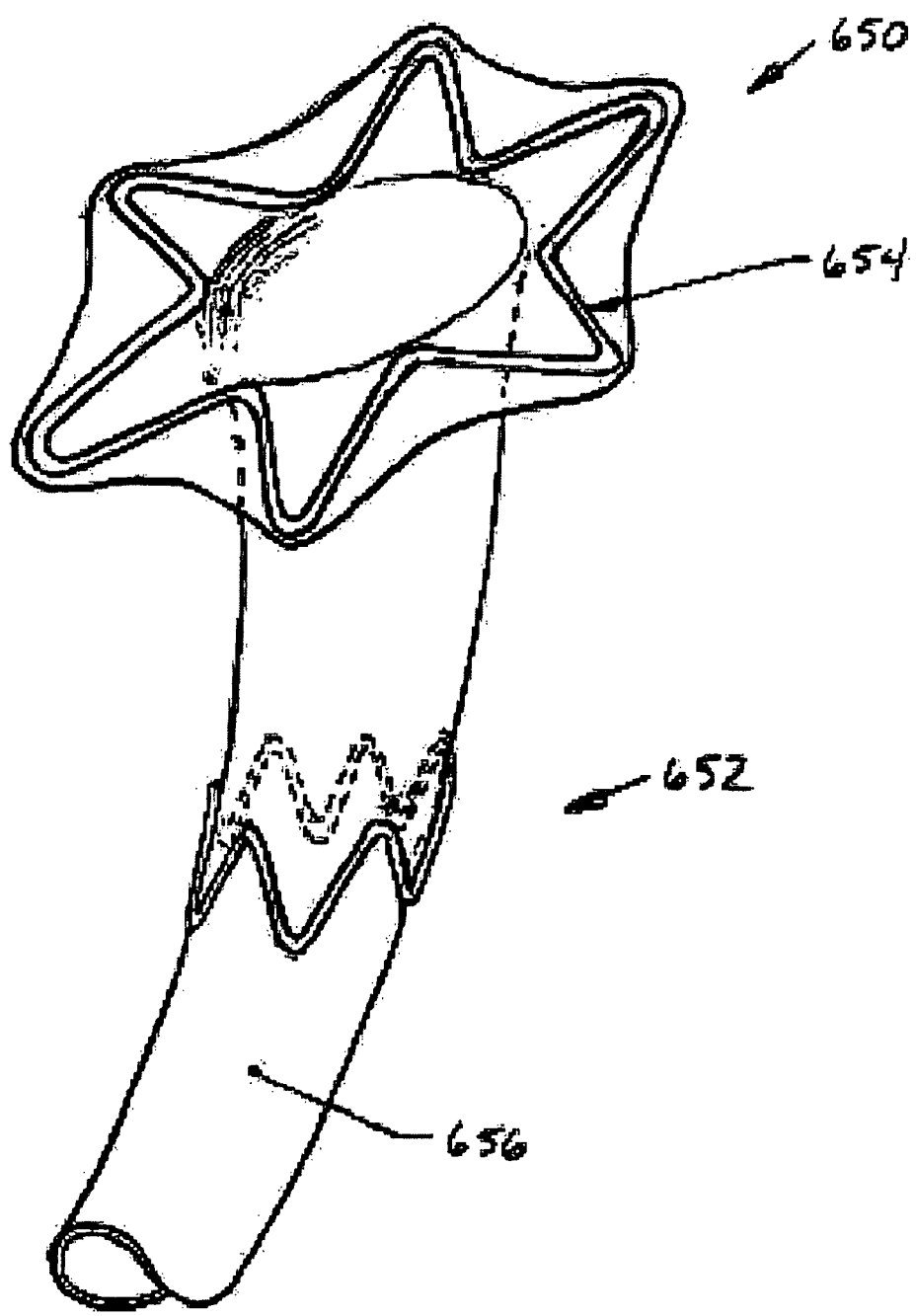
FIG. 6G illustrates an anchoring component according to another embodiment of the invention.

FIG. 6G illustrates an anchoring component according to another embodiment of the invention. Referring to FIG. 6G, a first anchoring component is generally depicted as reference number 650 and a second anchoring component is generally depicted as reference number 652. In the embodiment, the preferred material for fabricating the first and second anchoring components is a nitinol wire material. However, these components may be formed with a cut tube, a ribbon, and the like as known in the art. The preferred thickness of the anchoring elements ranges from about 0.2 to 0.5 mm or more.

The first anchoring component 650 illustrates a z-type anchoring component, e.g., a z-stent arranged in a substantially flat star pattern. More specifically, the first anchoring component 650 may be adjusted at an angle from a horizontal surface in range from about 0 degrees to 90 degrees, preferably, the angle ranges from about 0 degrees to 20 degrees. The anchoring component 650 includes a plurality of undulating elements 654, e.g., zig-zag elements, arranged around the circumference of the sleeve 656. The undulating elements 654 have a height and a width as previously described with reference to FIG. 6E. The second anchoring component 652 illustrates a z-type anchoring component as previously described with reference to FIGS. 6D and 6E. The first and second anchoring components may be separated by a distance ranging from about 2 to 60 mm or more. In a preferred embodiment, the first anchoring component 654 is positioned at the stomach antrum and the second anchoring component 652 is positioned on an opposite side of the pylorus in the duodenal bulb. Other locations as described in FIGS. 10A to 10D have also been contemplated.

Figure 6H:
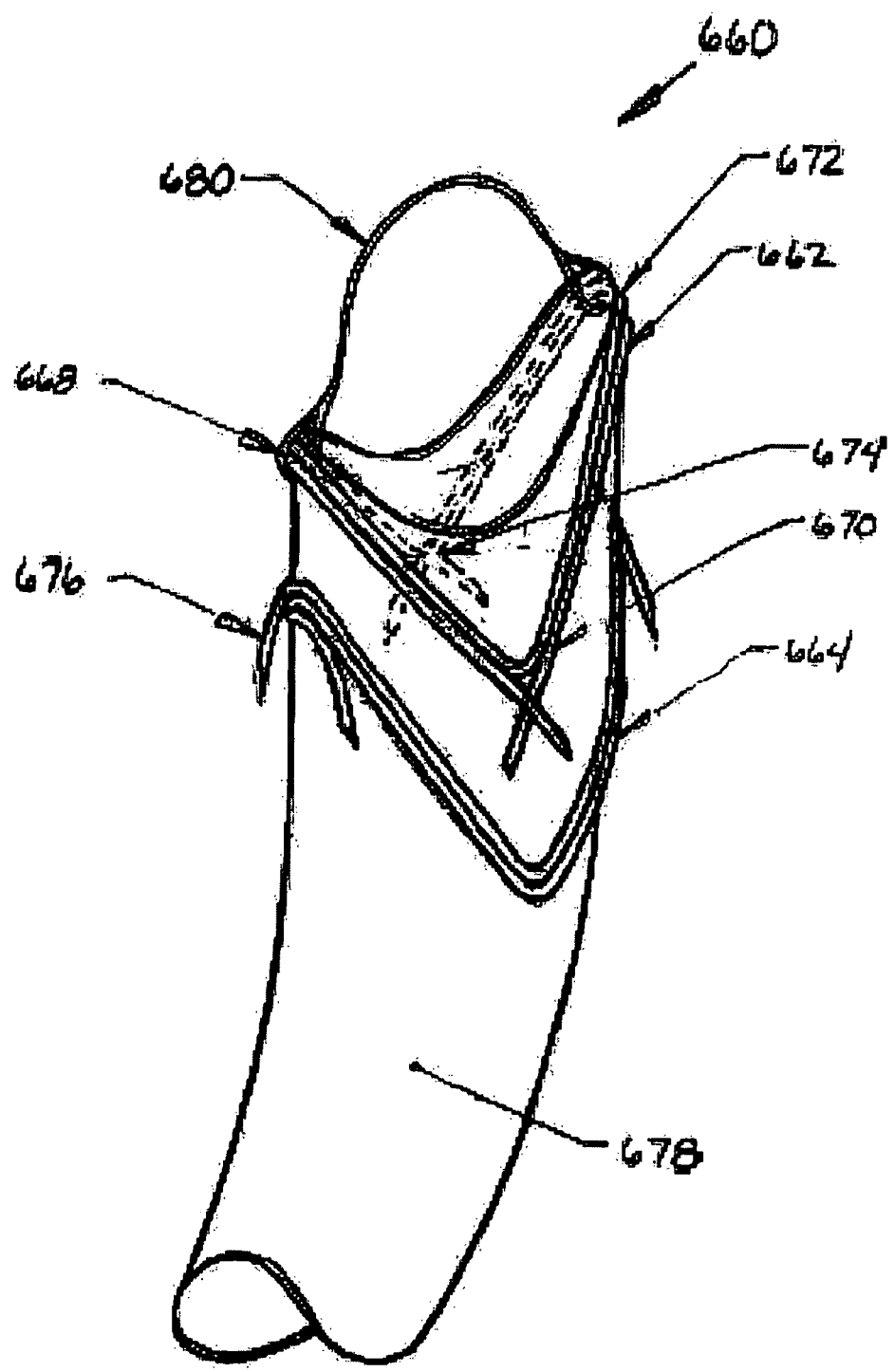
FIG. 6H illustrates an anchoring component according to another embodiment of the invention.
Figure 6L:
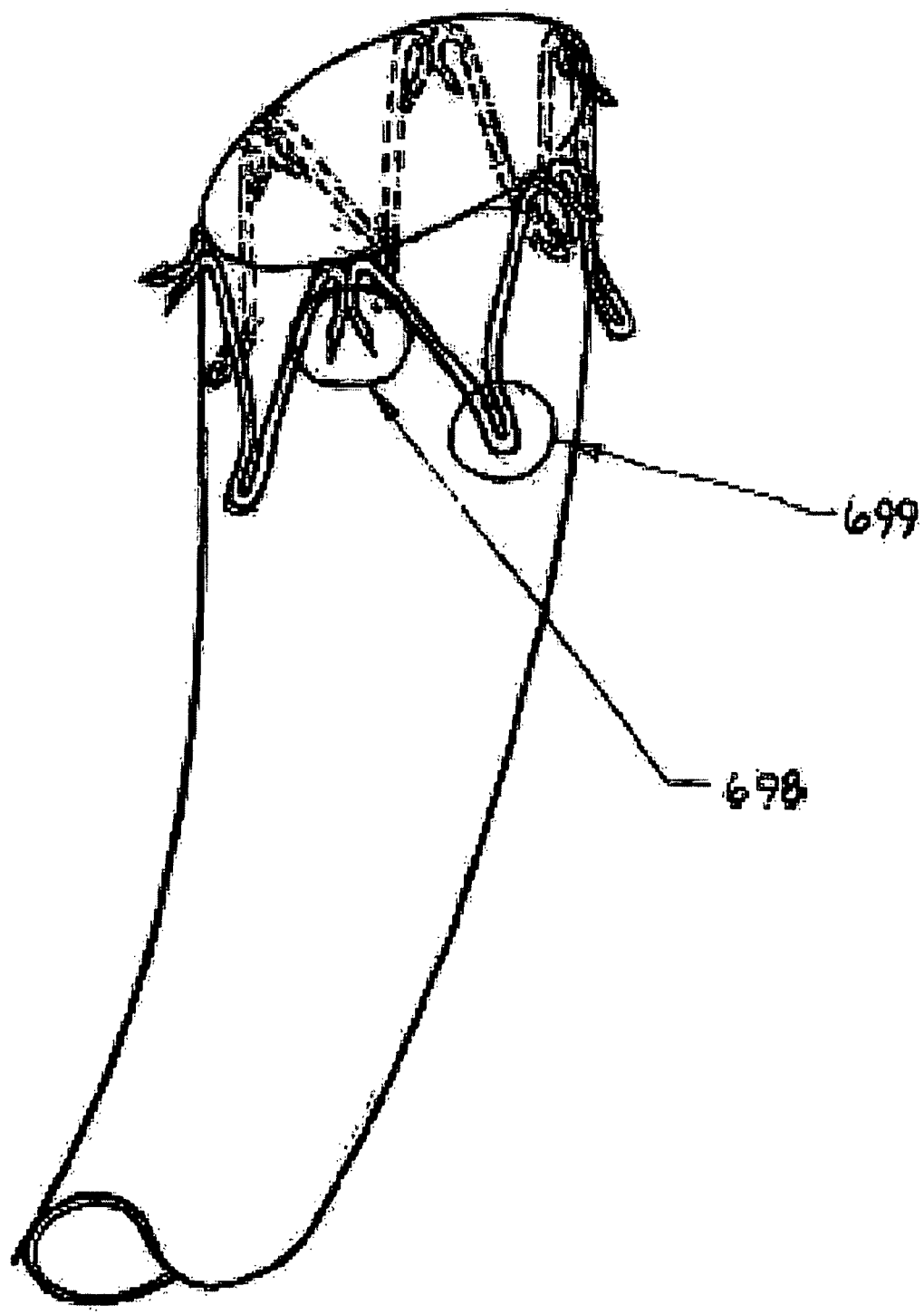
FIG. 6L illustrates active and passive anchoring elements according to another embodiment of the invention.

FIG. 6H illustrates an anchoring component according to another embodiment of the invention. Referring to FIG. 6H, an anchoring component is generally depicted as reference number 660. Preferably, the anchoring component 660 includes a first anchor element 662 and a second anchor element 664. Of course, there may be more than two anchor elements along the length of the sleeve, for example, multiple elements can be arranged along the length of the sleeve, thereby providing a longer supported length. The anchoring component 660 has a cylindrical shape. Of course, the anchoring element may be configured into a number of different geometric shapes, e.g., a conical, tapered, flat flange, and the like.

The spacing between the first element 662 and the second element 664 can be adjusted for the desired flexibility of the sleeve in the anchored portion. Preferably, the spacing between the elements ranges from about 2 mm to 30 mm more. More preferably, the spacing ranges from about 10 to 20 mm.

The first element 662 includes a first apex 668, a second apex 670, a third apex 672, and a fourth apex 674 and the second element 664 also includes four apices. The apices are formed by one or more wires incorporated into each element. In this configuration, the wire diameter ranges from about 0.2 to 0.5 mm or more. One of the wire ends 676 is oriented to point in the distal direction of the sleeve 678, thereby forming an anchor element. The anchor elements are designed to prevent migration of the device.

A tether line 680 may be arranged between opposing apices, thereby allowing for a single grasp retrieval location. For example, upon pulling the tether line 680 the anchoring component may be removed. The tether line 680 causes the opposing apices to be drawn toward each other such that the first element 662 can be pulled into an oversized removal tube (not shown). In a preferred embodiment, the wire ends forming the anchoring elements are oriented such that they naturally release from the tissue as the device is pulled by the tether line 680. It is also possible to include multiple tether lines, for example, the second element 664 may also have a tether line (not shown) between opposing apices.

FIG. 6I illustrates an anchoring component according to another embodiment of the invention. FIG. 6J illustrates an enlarged view of a portion of the anchoring component shown in FIG. 6I in an undeployed configuration. FIG. 6K illustrates an enlarged view of a portion of the anchoring component shown in FIG. 6I during a deployment configuration.

Referring to FIGS. 6I to 6K, an anchoring component is generally depicted as reference number 682. The anchoring component 682 includes a plurality of undulating elements 684, with each undulating element including a first apex 686, a second apex 688, and a third apex 690. Each of the undulating elements 684 includes a height and a width as previously explained with reference to FIG. 6E.

A second undulating element 692 is connected to the undulating element 684 with a flexible connection bridge 694. The second undulating element 692 is separated by a distance ranging from about 2 mm to 10 mm or more. The second undulating element 692 is a mirror image of its adjacent undulating element 684. The anchoring component is preferably formed from a flexible, elastic, or pseudo elastic material, and more preferably the material is nitinol. In the embodiment, the anchoring component is formed from a cut nitinol tube having a thickness ranging from about 0.05 mm to 2 mm or more.

During a thermal setting process an adjacent undulating element is folded back and arranged on the other undulating element as shown in FIG. 6K. After the thermal setting process the resultant anchoring component is double walled as shown in FIG. 6I. A sleeve 696 is attached to an inner wall of the anchoring component 682.

When the anchoring component 682 is loaded on the delivery tube of the invention it is unfolded as shown in FIG. 6J and radially crushed and constrained with a sheath. During deployment and release of the sheath one of the undulating elements not attached to the sleeve 696 re-folds to form the double wall anchoring component 682 as shown in FIGS. 6I and 6K. The double wall provides significant radial hoop strength without significantly compromising delivery profile. Other geometric configurations of the undulating elements have also been contemplated. Moreover, additional adjacent undulating elements may also be used. For example, there may be two or more rows of undulating elements as the number of undulating element rows increases the overall strength of the anchoring component increases.

FIG. 6L illustrates active and passive anchoring elements according to another embodiment of the invention. Referring to FIG. 6L, an anchoring component includes active anchoring elements 698 and passive anchoring elements 699. An active anchoring element is designed to at least partially penetrate a portion of anatomy. A passive anchoring element is designed to not penetrate a portion of an anatomy, but rather have a region designed to engage with a portion of the anatomy. Any combination or number of active anchoring elements 698 and passive anchoring elements 699 may be used with any of the anchoring components described herein.

The active anchoring element 698 may include a substantially pointed region to partially penetrate a portion of anatomy, e.g., terminated wire region of the anchoring component. Preferably, the active element 698 is formed into a barb-like element that provides a way to attach it to a patient's anatomy. The active elements 698 may be formed along any portion of the anchoring component. Preferably, the active elements 698 are formed at or near an apex of the anchoring component as shown in FIG. 6H. Passive elements 699 include a protrusion of the anchoring component. The passive elements 699 may be formed along any portion of the anchoring component. Preferably, the passive elements 699 is formed at or near an apex of the anchoring component as shown in FIG. 6F.

The active and/or passive elements provide a mechanism to prevent migration of the device. Of course, other geometries as known in the art may be utilized with any of the active and/or passive anchoring elements to provide a fixation mechanism. In addition, an anchoring component may include any combination of active and passive elements.

FIG. 7 illustrates a medical device according to another embodiment of the invention. Referring to FIG. 7, the medical device is generally depicted as reference number 700. The medical device includes a first anchoring component 702 and a second anchoring component 704. The first anchoring component 702 and the second anchoring component 704 are described with reference to FIG. 6F. The second anchoring component 704 is separated from and arranged upside down relative to the first anchoring component 702. The separation ranges from about 2 mm to 60 mm or more, and more preferably, the anchoring components are separated by a distance ranging from about 20 to 40 mm. In addition, there is optionally a radiopaque strip 708 arranged longitudinally along the length of the sleeve 706.

FIG. 8 illustrates a deployment flowchart according to another embodiment of the invention. FIGS. 9A-9G illustrate a deployment procedure according to another embodiment of the invention. Referring to FIG. 8 and FIGS. 9A to 9G, a flowchart 800 is used to depict typical steps used in the deployment of a device according to an embodiment of the invention. As previously discussed, the medical apparatus includes a device and a delivery tube. In operation, the medical apparatus is removed from packaging material. The packaging material typically provides a sterile environment for transporting the medical apparatus to various end users. Step 802:

Step 802 describes advancing an apparatus to a predetermined location. The predetermined location is typically located near the pylorus. Other locations are also possible, e.g., before, across, or after the pylorus; in the esophagus; at the gastroesophageal interface; in the stomach. For example, the anchoring component may be arranged prior to the pylorus, in the stomach antrum, across the pylorus, in the duodenum bulb, in the small intestine or at another suitable site.

The apparatus may either be utilized in a substantially adjacent fashion to the medical scope or positioned inside the working channel of the medical scope. For example, in one embodiment the apparatus may be coupled to the medical scope with a coupling unit to provide placement of the apparatus in a substantially adjacent configuration to the medical scope. More specifically, the coupling unit detachably couples the medical scope to the apparatus, e.g., in a substantially side-by-side configuration. The apparatus may be either arranged to the coupling unit prior to or after step 802. Other suitable techniques as known in the art are also possible.

The apparatus may also be positioned within a lumen of the medical scope, e.g., a working channel of the medical scope. The positioning within the working channel of the medical scope may be accomplished prior to or after step 802. In a preferred embodiment, a leading edge of the delivery tube is aligned with and inserted into an access port of the working channel of a medical scope, e.g., an Olympus GIF-X7Q160 endoscope (available from Olympus America, Inc. of Center Valley, Pa.). The delivery tube including the device is advanced until a tip of the device extends just beyond the viewing end of the endoscope.

Figure 9A:
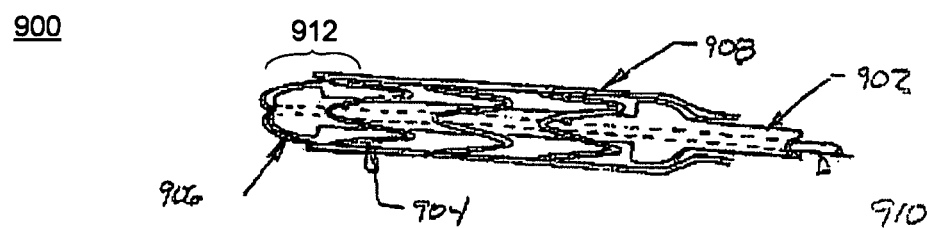

Step 804:

Step 804 describes adjusting the pressure source to a deployment pressure after the apparatus is advanced to the predetermined location. FIG. 9A illustrates a cross-sectional view of the apparatus positioned at a deployment location. It is noted that the cross-sectional view is independent of either the medical scope or coupling unit for clarity. Referring to FIG. 9A, the apparatus is generally depicted as reference number 900. The apparatus includes a delivery tube 902, and an anchoring component 904 positioned between the two fixing components 906 and captured within the sheath 908. As clearly indicated, the sleeve 910 is inverted inside a lumen of the delivery tube 902.

Deployment of the sleeve is initiated by adjustment of an external pressure source that has been connected to the delivery tube 902. The external source includes fluid such as a liquid, gas or a combination thereof. Preferably, the fluid is a saline solution of radiopaque contrast and saline. A pressurization device such as a perfusion bag, syringe, or the like, containing the fluid is attached to the hub end of the delivery tube (not shown). As previously explained the pressurization device may be attached to a connector or other attachment mechanism in communication with the delivery tube. The pressure of the pressurization device is then increased to approximately 200 mmHg to 300 mmHg or greater before a valve is opened to release the fluid.

Figure 9B:
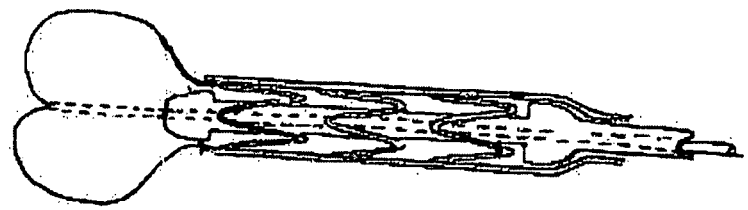
Figure 9C:
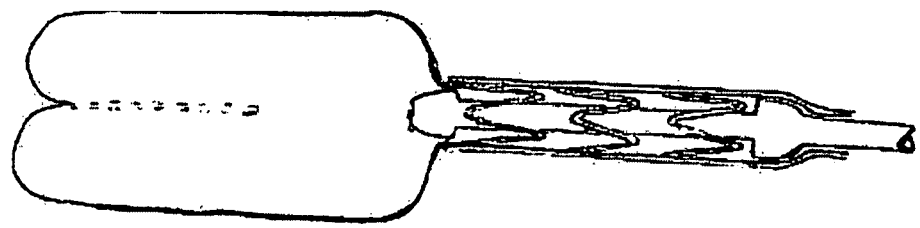
Figure 9D:
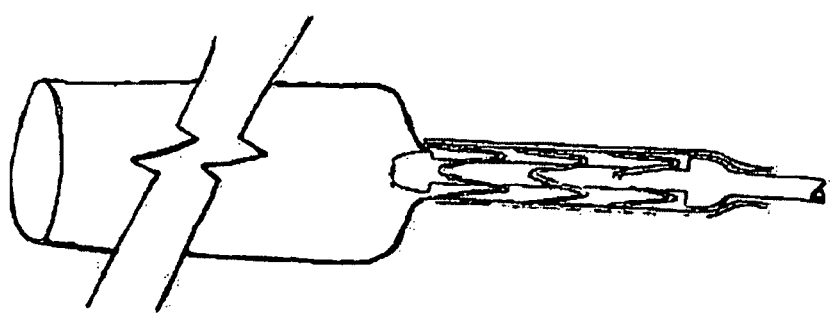

Step 806:

Step 806 describes deploying the sleeve. Referring now to FIG. 9B, the valve is opened to release the fluid from the perfusion bag. As the fluid reaches the end of the delivery tube 902 via the lumen the sleeve 910 deploys by everting from a distal portion 912 of the delivery tube 902. The everting process may be monitored by fluoroscopy or other techniques as known in the art. As the sleeve deploys, pressure in the perfusion bag is maintained by adding additional air into the bladder side using a hand inflator. As shown in FIGS. 9C to 9D, the sleeve deployment continues until full eversion is complete and a pressured fluid, e.g., contrast solution, flushes through the sleeve signaling completion of the sleeve eversion. Everting enables the sleeve to track tortuous anatomies while permitting full deployment of the sleeve. Everting also permits deployment of the sleeve from a position not extending significantly beyond the pylorus. That is, the apparatus permits sleeve deployment from a location proximal to the furthest distal final location of the sleeve.

Steps 808 and 810:

Steps 808 and 810 describe positioning an apparatus for deploying the anchoring component and deploying the anchoring component. After deploying the sleeve a distal end of the medical scope and remaining apparatus components are positioned to the target anchoring position for deploying the anchoring component. The target anchoring position may be the esophagus, the gastroesophageal interface, the stomach, the small intestine. For example, the target anchoring position may be prior to the pylorus, stomach antrum, across the pylorus, after the pylorus, the duodenal bulb, the small intestine, or another suitable site for placement of the sleeve and anchoring component.

Now referring to FIGS. 9E-9G, the deployment of the anchoring component 904 is accomplished by retraction of the sheath 908, thereby permitting deployment of the anchoring component 904, e.g., elastic self-expanding stent. After the sheath 908 has been fully reversed, the anchoring component 904 is fully deployed. In another embodiment, a push-rod may be used to slidably deploy the anchoring component out a distal end portion of the delivery tube. In addition, a balloon may be utilized to seat and/or deploy the anchoring component 904.

Step 812:

After the anchoring component has been deployed, confirmation of accurate deployment and removal of the medical scope is accomplished in step 812. As shown, in FIG. 9G, the medical scope and delivery tube 902 and sheath 908 are removed. Confirmation of accurate deployment is accomplished by means known in the art, for example, endoscopic visualization, ultrasound visualization, fluoroscopic visualization and the like.

Figure 10A:
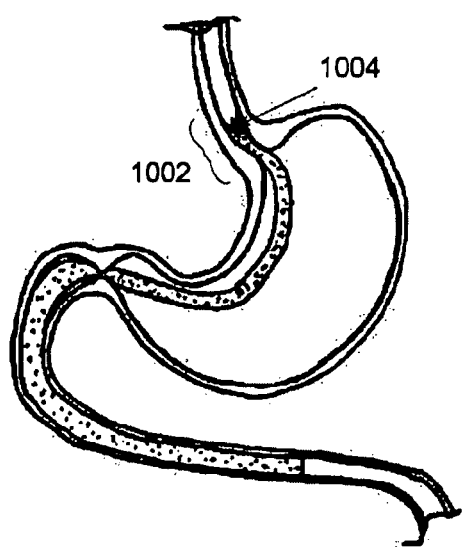
FIGS. 10A-10D illustrate anchor component placements according to embodiments of the invention.
Figure 10B:
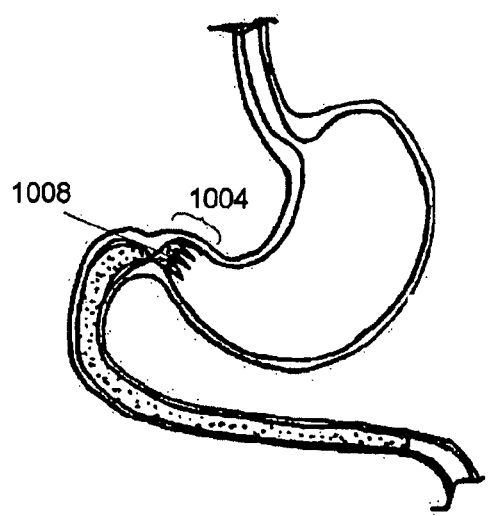
Figure 10C:
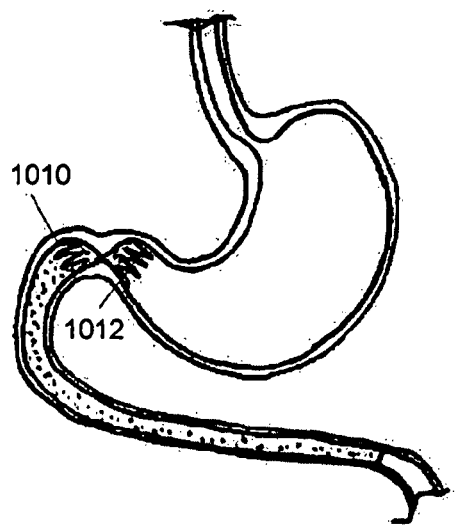
Figure 10D:
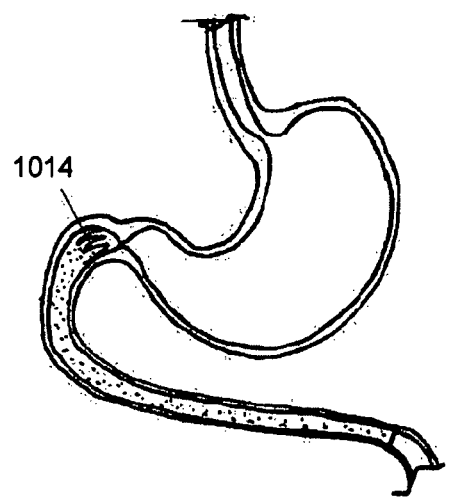

FIGS. 10A-10D illustrate anchor and sleeve deployment placements according to various embodiments of the invention. Referring to FIG. 10A, after step 808 the apparatus is reversed to the gastroesophageal interface 1002 where the anchoring component 1004 is deployed as described in step 810. Referring to FIG. 10B, the apparatus is reversed to the stomach such as prior to the pylorus, e.g., stomach antrum 1006 where the anchoring component 1008 is deployed as described in step 810. Referring to FIG. 10C, a first anchoring component 1010 is deployed in the duodenum bulb as described with reference to step 810, then the apparatus is reversed and a second apparatus 1012 is deployed as described in step 810 at the stomach antrum. Referring to FIG. 10D, the anchoring component 1014 is deployed in the duodenal bulb.

EXAMPLES

Without intending to limit the scope of the invention, the following examples illustrate how various embodiments of the invention may be made and/or used.

Example 1

This example illustrates the manufacture of a sleeve and an anchoring component according to an aspect of the invention. A substantially non-porous composite film including ePTFE with a thermal adhesive layer of FEP on one side was used. The composite film possessed the following properties: a width of about 25 mm, a thickness of about 0.0025 mm, an Isopropyl alcohol bubble point of greater than about 0.6 MPa, and a tensile strength of about 309 MPa in the length direction, e.g., the strongest direction.

Four film strips about 25 mm wide were laid down in the longitudinal direction, arranged evenly around a 25 mm diameter mandrel having a length of about 150 cm. The FEP side of the film was oriented up or away from the mandrel. Temporary adhesive tape was used to secure the ends of the four longitudinal film strips to the mandrel.

The mandrel with the longitudinal oriented film was then covered with a helically wrapped film. The helical film was the same film type used in the longitudinal wrap. The FEP was oriented down towards the mandrel and against the longitudinal film. A helical wrapper was used to apply the film using a pitch of about 8 mm. The term pitch is the amount of advance per revolution of the mandrel. With a 25 mm wide film, a pitch of about 8 mm produces film to film overlap of about 17 mm. One complete pass of film was applied resulting in an overlapping helical layer having a thickness of four layers of film. The film ends were secured to the mandrel by wrapping the film in a circumferential fashion. The temporary tape used to secure the longitudinal layers was removed.

The film layered mandrel was then placed into an air convection oven set to about 320° C. for about 30 minutes. The composite sleeve was then removed from the mandrel resulting in a thin walled sleeve having a diameter of about 26 mm and a length of about 130 cm.

An anchoring component having a tapered helical configuration was formed from super elastic nitinol wire obtained from Fort Wayne Metals, Part No. 1755-0207. The Nitinol wire had a diameter of about 0.02 inches. The anchoring component was formed having a tapered configuration. More specifically, one end of the anchoring component had a diameter of about 26 mm and an opposite end had a diameter of about 40 mm.

In the manufacture, the nitinol wire was drawn around a winding jig, which acted to hold the wire in its desired shape during a thermal setting process. The jig was constructed of a stainless steel cylinder having a series of attachment pins around which the wire is wound. More specifically, the tapered winding jig had a small diameter of about 26 mm, a large diameter of 40 mm and a central taper, thereby joining the two diameters with length of about 4 cm. Protruding out of the tapered winding jig were pins having a diameter of about 1 mm. Ends of the wire were terminated under screw heads which held the wire in a position during the subsequent heat treatment step.

The wire jig was then placed in a convection oven at about 470° C. for about 15 to 20 minutes. Upon removal, the forming jig with the wire pattern was quenched in water at about ambient room temperature. After the jig was cooled and dried the terminating screws were loosened and the wire was removed from the jig.

The anchor component was then dipped into about a twenty percent solution of nitric acid at about 80° C. for about 30 minutes. The acid dip was followed by a water rinse. The wire ends of the anchoring component were then secured to adjacent wire portions of the anchoring component using an ePTFE CV-6 suture available from W.L. Gore and Associates, Inc, from Flagstaff, Ariz.

The finished anchoring component had a tapered, undulating shape formed from the wire. The anchoring component had a length of about 4 cm, a small diameter of about 26 mm and a large diameter of about 40 mm. A total of 6 apices per revolution were formed in the undulating wire of the anchoring component.

The sleeve from above was then radially distended by pulling it over a tapered mandrel. The tapered aluminum mandrel had about a 26 mm diameter section with an opposing about 40 mm diameter section. The 26 mm and 40 mm diameters sections were joined by about a 4 cm long tapered section. The tapered aluminum mandrel was then heated to about 320° C. in an oven for about thirty minutes. On one end of the sleeve, two pulling tabs were formed by removing about 0.12 inches of sleeve material away from the sides of the sleeve. With the mandrel heated to about 320° C. the sleeve was pulled onto the 26 mm diameter section and then over the tapered section onto the 40 mm diameter section. The sleeve was left in place on the heated mandrel for about 1 minute and removed. After trimming it to a length, the resulting sleeve had a 40 mm diameter end section of about 2 cm long, a tapered section of about 4 cm long and about a 26 mm diameter section being about 94 cm long.

The tapered anchoring component was then joined to the tapered portion of the sleeve. A tapered stainless steel cone adaptor was fabricated to aid in this process. The cone adaptor had an outside diameter of about 40 mm tapering to about 26 mm and inside diameter of about 26 mm. This cone adaptor was positioned onto about a 26 mm mandrel having a length of about 145 cm. The distended, tapered end of the sleeve was positioned onto an about 26 mm mandrel and over the about 40 mm diameter cone adaptor so that the tapered portion of the sleeve was positioned onto the tapered portion of the cone. The tapered anchoring component was then placed over the tapered portion of the sleeve. An ePTFE tape being about 9.7 mm wide having a FEP outer layer was then circumferentially wrapped over the anchoring component along the tapered 4 cm portion of the anchoring component. The ePTFE tape had a thickness of about 0.001 inches, a weight of less than about 0.288 gm/12 in$^2$ (12" long by 1" wide), and a minimum mean break strength of 5.0 kg/in. The FEP layer was then oriented down or against the anchoring component.

The mandrel and the wrapped assembly were then placed into an air convection oven set to about 320° C. for about 30 minutes. After cooling the sleeve and the anchoring component, they were removed from the mandrel and the sleeve was trimmed to a length of about 50 cm. The sleeve end with the anchoring component was also trimmed with a slight scallop configuration following the undulations of the anchor component.

The formed sleeve had a wall thickness of about 0.01 mm. The formed sleeve also exhibited very little compressive hoop strength; it was easily collapsed with near-zero external compressive force. The lubricity of the fluoropolymer materials of the formed sleeve combined with the thinness and flexibility of the sleeve also made it easy to evert and invert from the delivery tube.

Example 2

This example illustrates the loading of the anchoring component and sleeve of example 1 into a deployment tube of this example.

The sleeve in Example 1 was inverted, that is, at least a portion of the sleeve was partially turned inside out, i.e., where at least a portion of the external surface becomes an internal surface. More specifically, the end portion of the sleeve farthest away from the anchoring component was pushed through the anchoring component, thereby inverting at least a portion of the sleeve. Next, the sleeve was radially compressed with a radial compressor (Model G Balloon Wrapper, Blockwise Engineering, Phoenix, Ariz.) to a compacted diameter of about 1.5 mm. The compression die was set to about 70° C. with a pressure of about 827.4 kPa. The sleeve was radially compressed using about 50 mm longitudinal steps through a compression tool. The sleeve end closest to the anchoring component was compressed using a compression die of about 1.5 mm and heated to a temperature of about 70° C.

The delivery tube is used to facilitate the compaction and loading of the sleeve and anchoring component onto a delivery tube made of polyether block amide No. 72d Pebax® tubing. The delivery tube had an outer diameter of about 3.3 mm and an inner diameter of about 2.5 mm. The delivery tube was reinforced by about a 0.1 mm diameter stainless steel wire braid. The delivery tube had two protrusions or shoulders to longitudinally constrain the anchoring component. The tapered shoulders had a distance between them of about 5.7 cm. The proximal shoulder had an outer diameter of about 5.8 mm and the distal shoulder had an outer diameter of about 4.8 mm. The two shoulders were fused onto the catheter shaft at about 220° C. using shrink tubing as a compression member.

A series of pull lines were threaded through the proximal free wire apices of the anchoring component. These pull lines were then laced through the sheath. The delivery tube was back-loaded into the sheath and positioned with the pull lines on the outside of the delivery tube. The sheath was also made of polyether block amide No. 72d Pebax® tubing. The sheath had an inner diameter of about 6 mm tapering down to about 4 mm. The delivery tube was back loaded into the sheath. Next, the crimped and compacted end of the sleeve was threaded into a distal end of the delivery tube.

The pull lines were tensioned to align and maintain the anchoring component between the shoulders while the anchoring component was compacted. Using a radial compression die, the anchoring component was compacted to a diameter slightly less than the inner diameter of the sheath. The anchoring component pull lines and the delivery tube were then pulled together, drawing the compressed anchoring component and delivery tube into the sheath. The pull lines were then cut and removed, thereby unthreading the line from the wire apices.

A pull-knob was then attached to the proximal end (user end) of the sheath. During device deployment, this ergonomic knob will assist in the pull back of the sheath, which will free the anchoring component and allow it to self expand. In addition, a connector was added to the proximal end of the delivery tube.

Example 3

In this example, biodigestible anchoring components were fabricated and studied for their respective corrosive amount of weight loss over time in a simulated gastrointestinal environment.

More specifically, three 25.4 mm inner diameter balloon-expandable anchoring components were constructed. Each of the anchoring components had different biodigestible wire materials. An aluminum (4043) weld wire, chromalloy (4130) weld wire, and stainless steel (308) weld wire were used in the fabrication of the three different anchoring components. These different wires were readily available and obtained from a welding supply facility. Each of the three different wires had a diameter of about 1.6 mm.

In the process of forming the anchoring component, each of the three different wires were wrapped onto a stainless steel pin jig. The stainless steel pin jig had about a 25.4 mm diameter and was about 100 cm long. The stainless steel pin jig had a number pins each having a diameter of about 1.52 mm. The pins were arranged to provide a single-ring in a six-apex zig-zag pattern. More specifically, the six pins were arranged in a first row and another six pins were arranged in second row below the first row, thereby forming the zig-zag pattern. The center-to-center distance between the pins along the length of the jig was about 19.1 mm. After wrapping one of the wires around the stainless steel pin jig, the anchoring component was removed from the jig and the wire ends were trimmed. This process was repeated for all three wires, thereby forming three different anchoring components of three different materials.

Each anchoring component was weighed using a Mettler balance (model AE104, Switzerland) and the weight was recorded in Table I below. Next, each of the anchoring components was submerged into a separate glass jar containing about 50 ml of a solution designed to simulate human gastric juices. The 50 ml solution was made in accordance with USP 29 Gastric Fluid, Simulated, TS, which is readily available as known in the art. Initially the solution had a pH of about 1.2, which is a requirement per USP 29.

Each one of the anchoring components was placed into separate jars containing about a 50 ml solution that was maintained at about 37° C. throughout the course of the study. The jars were also placed on a shaker for agitation and each jar had lid with a small hole to provide a vent, e.g., for offgassing of the hydrogen. The shaker had a model name of IKA-VIBRAX-VXR S1, manufactured by Janke & Kunkel GmbH & Co, IKA Labortechnik, and model no. 718308.

Each of the anchoring components were rinsed and weighed on the days illustrated with the following procedure. An anchoring component was removed from the Gastric Fluid, Simulated, TS solution and rinsed in two separate about 150 mL deionized water baths. The anchoring component was placed in the first bath immediately followed by placing it in the second bath. After the second rinse, the anchoring component was dipped into about 50 mL of isopropyl alcohol and the sample was air-dried. When completely dried, the anchoring component was weighed and data recorded as shown in Table I below. The pH of the solution was also checked and recorded to ensure there was a reaction occurring at various times throughout the study as indicated in Table I. In addition, the asterisk notation on days 2 through 14 denotes the days in which the USP 29 Gastric Fluid, Simulated, TS was replaced with a fresh solution for each 50 mL jar holding each anchoring component. The sample was then returned to its containers and subjected to time another cycle. This recording process was repeated for each anchoring component using new deionized water baths and isopropyl alcohol bath. The results of the study are illustrated in Table I and II below.

TABLE I

| Anchoring Component Type | Day 1 | Day 2* | Day 3* | Day 4* | Day 7* | Day 8* | Day 10* | Day 12* | Day 15 |
|---|---|---|---|---|---|---|---|---|---|
| Stainless Steel anchor component | — | — | — | — | — | — | — | — | — |
| 50 ml gastric solution (pH) | — | 1.20 | 1.11 | 1.09 | 1.08 | 1.06 | 1.39 | 1.35 | 1.17 |
| Mass (g) (initial mass 4.70 g) | 4.70 | — | — | — | 4.70 | — | — | — | 4.70 |
| Aluminum anchor component | — | — | — | — | — | — | — | — | — |
| 50 ml gastric solution (pH) | — | 1.27 | 1.33 | 1.14 | 2.73 | 1.27 | 2.28 | 2.33 | 3.29 |
| Mass (g) (initial mass 1.51 g) | 1.51 | — | — | — | 1.44 | — | — | — | 1.31 |
| Chromalloy anchor component | — | — | — | — | — | — | — | — | — |
| 50 ml gastric solution (pH) | — | 1.31 | 1.25 | 1.19 | 4.60 | 1.23 | 3.00 | 4.00 | 4.40 |
| Mass (g) (initial mass 4.54 g) | 4.54 | — | — | — | 4.32 | — | — | — | 3.91 |

TABLE II

| Anchoring Component Type | Total Mass Loss | Percent Mass Loss |
|---|---|---|
| Stainless Steel anchor component | 0.00 g | 0.00% |
| Aluminum anchor component | 0.20 g | 13.25% |
| Chromalloy anchor component | 0.63 g | 13.88% |

Now referring to Table II, which summarizes each of the anchoring components and their respective degree of weight loss it can be shown that the weight loss occurred at different rates throughout the study. In addition, degradation of the anchoring component was also visually observed throughout the study. More specifically, corrosion grooves in the anchoring components that exhibited weight loss was observed. In addition, the corrosion was particularly noticeable around the apices of the anchoring components.

From this data, weight, mass, and strength loss of the anchoring components may be substantially tailored by choice of material and the anchoring components respective displacement reaction, i.e., metal+acid==>metal salt+hydrogen and/or predesigned larger surface area into predetermined locations that promote faster weight loss, i.e., by creating a larger surface area. The respective corrosion mechanism reaction are known in the art. As a result, material corrosive selectively and surface area exposure designs may be used to provide areas that are more susceptible to corrosion.

Test Method:

This section describes measuring the tensile strength of the film. The tensile peak force was measured and averaged for ten samples using an Instron Model No. 5560 tensile testing machine (Canton, Mass.) equipped with Series 2714 Cord and Yarn grips. The jaw separation was 10.2 cm and the cross-head speed was 200 mm/min. The average of ten peak force measurements was used. The average of ten sample widths was calculated. Thickness was measured with Mitutoyo Snap Gage Model No 547-400 (Nakatsugawa, Japan). The average of ten thickness measurements was used. Tensile strength was calculated as the quotient of tensile peak force and cross-sectional area of the tested samples.

Isopropyl alcohol (Univar, Kirkland, Wash.) bubble point measurements were performed in accordance with the general teachings of ASTM E128-99. The tests were performed using about a 2.54 cm diameter test fixture. Pressure was increased at about 1.4 kPa/sec. The pressure corresponding to the appearance of the first stream of bubbles was identified as the bubble point. Isopropyl alcohol bubble point measurements above about 0.6 MPa were not reliable due to test equipment limitations. Bubble point values represent the average of five measurements.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A medical apparatus comprising:
   a device including:
   a radially compressed sleeve; and
   an expandable anchoring component attached to at least a portion of said sleeve; and
   a delivery tube having a first lumen and a second lumen, said first lumen being configured as an inflation port to deploy said sleeve, wherein said sleeve is substantially fully inverted and contained within said second lumen,
   wherein said expandable anchoring component is arranged on a distal portion of said delivery tube,
   wherein at least a portion of said anchoring component is covered with a sheath, and
   wherein said radially compressed sleeve has a reduced profile so as to have a diameter that is substantially smaller than a diameter of said second lumen.

2. The medical apparatus of claim 1, wherein the delivery tube is configured to fit inside a working channel of an endoscope.

3. The medical apparatus of claim 2, wherein said working channel of said endoscope has a diameter of about 10 mm or less.

4. The medical apparatus of claim 1, further comprising a connector removably coupled to a proximal end of said delivery tube.

5. The medical apparatus of claim 1, wherein said sheath is removably coupled to the distal portion of said delivery tube.

6. The medical apparatus of claim 1, wherein said anchoring component comprises a nickel titanium alloy.

7. The medical apparatus of claim 1, wherein said anchoring component comprises a biodigestible material.

8. The medical apparatus of claim 1, wherein said anchoring component comprises a radiopaque material.

9. The medical apparatus of claim 1, wherein said anchoring component has a tapered helical pattern.

10. The medical apparatus of claim 1, wherein said anchoring component includes at least one of a passive anchoring element and an active anchoring element.

11. The medical apparatus of claim 1, wherein said anchoring component is at least partially covered with a thermoplastic material.

12. The medical apparatus of claim 1, wherein the anchoring component comprises a bioabsorbable material.

13. The medical apparatus of claim 1, wherein said delivery tube comprises a thermoplastic material.

14. The medical apparatus of claim 13, wherein said thermoplastic material comprises nylon.

15. The medical apparatus of claim 14, wherein said nylon comprises a polyether block amide.

16. The medical apparatus of claim 1, wherein said sleeve comprises a fluoropolymer.

17. The medical apparatus of claim 16, Therein said fluoropolymer comprises polytetrafluoroethylene.

18. The medical apparatus of claim 17, wherein said polytetrafluoroethylene comprises expanded polytetrafluoroethylene.

19. The medical apparatus of claim 1, wherein said sleeve comprises fluorinated ethylene, propylene.

20. The medical apparatus of claim 1, wherein said sleeve has a tapered configuration.

21. The medical apparatus of claim 1, further comprising a balloon for expansion of said anchoring component.

22. The medical apparatus of claim 1, wherein said sleeve comprises markings indicating length graduations.

23. The medical apparatus of claim 1, wherein said sleeve comprises a radiopaque material.

24. The medical apparatus of claim 1, wherein said fixing components are positioned on a distal portion of the delivery tube.

25. The medical apparatus of claim 1, further comprising a sheath circumferentially covering at least a portion of said anchoring component.

26. The medical apparatus of claim 1, further comprising a sheath circumferentially covering substantially the entirety of the delivery tube.

27. The medical apparatus of claim 26, wherein said sheath extends beyond a distal end of said delivery tube.

28. The medical apparatus of claim 26,
   wherein said sheath has a tapered portion arranged over of said fixing components.

* * * * *